United States Patent
Bayer et al.

(10) Patent No.: US 10,105,498 B2
(45) Date of Patent: Oct. 23, 2018

(54) DRIVE MECHANISM OF A DRUG DELIVERY DEVICE

(71) Applicant: Sanofi, Paris (FR)

(72) Inventors: Stefan Bayer, Würselen (DE); Daniel Berning, Baesweiler (DE); Philippe Blank, Düsseldorf (DE); Wolfgang Pelzer, Kreuzau (DE); Björn Wilden, Simmerath (DE)

(73) Assignee: Sanofi, Paris (FR)

( * ) Notice: Subject to any disclaimer, the term of this patent is extended or adjusted under 35 U.S.C. 154(b) by 44 days.

(21) Appl. No.: 14/783,496

(22) PCT Filed: Apr. 8, 2014

(86) PCT No.: PCT/EP2014/056975
§ 371 (c)(1),
(2) Date: Oct. 9, 2015

(87) PCT Pub. No.: WO2014/166897
PCT Pub. Date: Oct. 16, 2014

(65) Prior Publication Data
US 2016/0074594 A1    Mar. 17, 2016

(30) Foreign Application Priority Data

Apr. 10, 2013 (EP) .................................... 13163075

(51) Int. Cl.
*A61M 5/315* (2006.01)
*A61M 5/20* (2006.01)
*A61M 5/31* (2006.01)

(52) U.S. Cl.
CPC .......... *A61M 5/31583* (2013.01); *A61M 5/20* (2013.01); *A61M 5/31541* (2013.01);
(Continued)

(58) Field of Classification Search
CPC ...... A61M 15/0065; A61M 2005/3154; A61M 2005/3152; A61M 2005/3126;
(Continued)

(56) References Cited

U.S. PATENT DOCUMENTS 6,193,698 B1* 2/2001 Kirchhofer ....... A61M 5/31551
604/207
6,446,627 B1 9/2002 Bowman et al.
(Continued)

FOREIGN PATENT DOCUMENTS

CN    10126899    3/2007
CN    101094699    12/2007
(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.
(Continued)

*Primary Examiner* — Emily Schmidt
*Assistant Examiner* — Alexandra Lalonde
(74) *Attorney, Agent, or Firm* — Fish & Richardson P.C.

(57) ABSTRACT

A drug delivery device for dispensing of a dose of a medicament includes a housing extending in an axial direction and a piston rod to operably engage with a piston of a cartridge to displace the piston in an axial distal direction. The drug delivery device includes a dose indicating mechanism including a first spool and a second spool rotatably supported in the housing and a dose indicating tape coiled onto at least the second spool and fixed with an end to an outer circumference of the first spool. The first and second spools are oriented substantially parallel to each other and substantially parallel to the piston rod.

17 Claims, 15 Drawing Sheets

(52) U.S. Cl.
CPC ....... *A61M 5/31553* (2013.01); *A61M 5/3157* (2013.01); *A61M 2005/3126* (2013.01); *A61M 2005/3154* (2013.01); *A61M 2205/581* (2013.01); *A61M 2205/582* (2013.01)

(58) Field of Classification Search
CPC .. A61M 5/31583; A61M 5/20; A61M 5/3155; A61M 5/31553; A61M 5/3157; A61M 5/31548; A61M 5/31541; A61M 2005/3125; A61M 15/0078; A61M 15/0066; A61M 5/31551; A61M 5/31533; A61M 5/31528; A61M 5/31555; A61M 5/3158; A61M 5/31585
See application file for complete search history.

(56) References Cited

U.S. PATENT DOCUMENTS

| | | | |
|---|---|---|---|
| 2003/0160072 A1* | 8/2003 | Geiser | A61M 5/24 222/327 |
| 2004/0244794 A1* | 12/2004 | Richards | A61K 9/0075 128/203.15 |
| 2004/0267207 A1 | 12/2004 | Veasey et al. | |
| 2005/0177114 A1* | 8/2005 | Michel | A61M 5/31553 604/207 |
| 2006/0153693 A1 | 7/2006 | Fiechter et al. | |
| 2008/0051713 A1 | 2/2008 | Kohlbrenner et al. | |
| 2008/0306445 A1 | 12/2008 | Burren et al. | |
| 2011/0054412 A1 | 3/2011 | Eich et al. | |
| 2011/0283997 A1* | 11/2011 | Walsh | A61M 15/0065 128/200.23 |

FOREIGN PATENT DOCUMENTS

| | | | |
|---|---|---|---|
| CN | 100443128 | 12/2008 | |
| CN | 102014991 | 4/2011 | |
| CN | 102892448 | 1/2013 | |
| WO | WO 2004/020028 | 3/2004 | |
| WO | WO 2004/078239 | 9/2004 | |
| WO | WO 2006/079481 | 8/2006 | |
| WO | WO 2007/030957 | 3/2007 | |
| WO | WO 2011/144326 | 11/2011 | |
| WO | WO 2013156224 A1 * | 10/2013 | ........ A61M 5/31541 |

OTHER PUBLICATIONS

International Preliminary Report on Patentability in International Application No. PCT/EP2014/056975, dated Oct. 13, 2015, 7 pages.
International Search Report and Written Opinion in International Application No. PCT/EP2014/056975, dated Jun. 4, 2014, 13 pages.

* cited by examiner

A-A

B-B

C-C

D-D

E-E

F-F

G-G

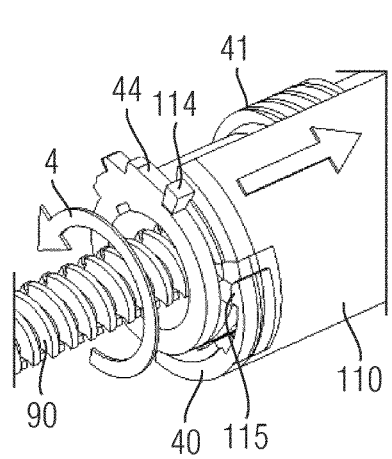
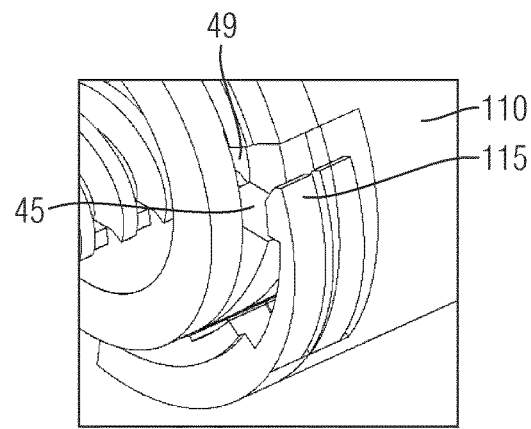
Fig. 24        Fig. 24a
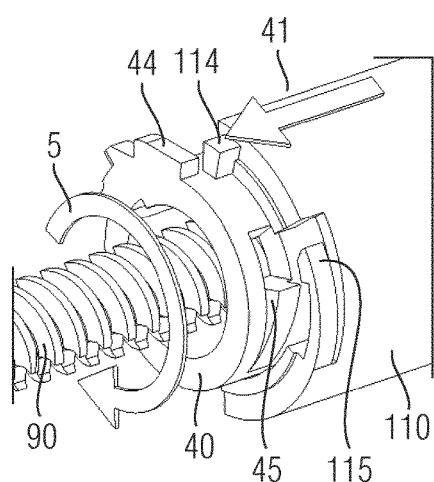
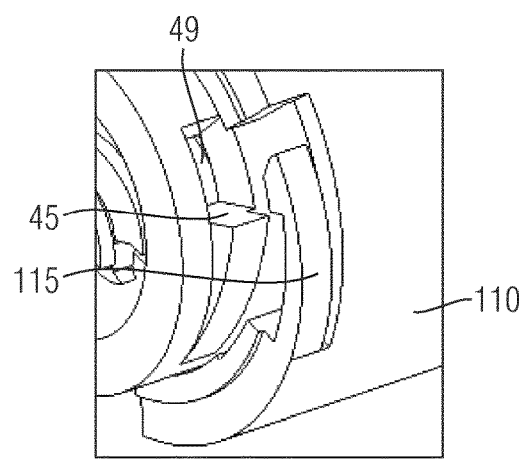
Fig. 25        Fig. 25a

DRIVE MECHANISM OF A DRUG DELIVERY DEVICE

CROSS REFERENCE TO RELATED APPLICATIONS

This application is a National Stage application under 35 U.S.C. § 371 of International Application No. PCT/EP2014/056975, having an International Filing Date of Apr. 8, 2014, which claims the benefit of European Application No. 13163075.8 filed Apr. 10, 2013. This disclosure of the prior applications are considered part of (and are incorporated by reference in) the disclosure of this application.

The present invention relates to a drive mechanism for a drug delivery device and to a respective drug delivery device. In particular, the invention relates to an injection device such like a pen-type injector inter alia comprising a single and/or a last-dose limiting mechanism and further comprising a comparatively large dose indicating display.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, which is adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

With such multi-dose drug delivery devices at least a last dose limiting mechanism is required to inhibit setting of a dose exceeding the amount of medicament left in the cartridge. This is to avoid a potentially dangerous situation for the user believing that a set dose is entirely injected. There already exist some drug delivery devices with end-of-content mechanisms or last dose mechanisms.

Drug delivery devices such like pen type injectors also provide a dose indicating mechanism which is operable to display the size of a set dose to a user. Typically, the housing of such drug delivery devices comprises a dose indicating window in which a number representing the size of the dose shows up.

Especially with elderly patients or users suffering impaired vision, reading of such dose indicating numbers is sometimes difficult. With devices adapted for injection of e.g. insulin, typical dose sizes may vary between 0 and 120 I.U. (International Units) of insulin. Due to the rather compact design and limited geometrical dimensions of typical drug delivery devices the size of such dose indicating numbers is fairly small. For visually impaired persons correct reading of comparatively tiny numbers may therefore be rather difficult. However, since such drug delivery devices are intended for self-medication treatment, it is of importance, that the user is able to correctly determine the size of dose actually set.

OBJECTS OF THE INVENTION

It is therefore an object of the present invention to avoid disadvantages of known drug delivery devices and to provide a drive mechanism of a drug delivery device allowing for an intuitive operation, both for setting and for dispensing of a dose. It is another object to provide a dose indicating mechanism which is easy and unequivocal to read even for persons suffering impaired vision.

In another object, the invention serves to provide a drive mechanism of a drug delivery device for setting and dispensing of a dose of a medicament and further featuring a single and/or a last dose limiting mechanism. Moreover, the drive mechanism should be rather compact to limit the overall size of the drug delivery device.

It is a further aim to provide a drug delivery device comprising such a drive mechanism and comprising a cartridge sealed with a piston and being operably engaged with a piston rod of such drive mechanism. The drug delivery device should be rather easy and intuitive to handle.

SUMMARY OF THE INVENTION

In a first aspect a drive mechanism of a drug delivery device is provided for dispensing of a dose of a medicament. The drive mechanism comprises an elongated housing extending in an axial direction. The housing is of substantially tubular or cylindrical shape that allows gripping and operating of the drive mechanism and of the drug delivery device by only one hand of a user.

The drive mechanism further comprises a piston rod to operably engage with a piston of a cartridge containing the medicament to be dispensed by the drive mechanism. The cartridge comprises a piston at its proximal end, which, by means of a displacement in axial distal direction serves to expel an amount of the medicament from the cartridge. The piston typically seals the cartridge in axial proximal direction.

The piston rod of the drive mechanism serves to displace the piston of the cartridge in axial distal direction for expelling a predefined amount of the medicament from the cartridge. Hence, the piston rod is operable to apply distally-directed thrust or pressure to the piston of the cartridge for displacing the same in distal direction for a predetermined distance that corresponds to a respective amount or dose of the medicament to be dispensed.

Furthermore, the drive mechanism comprises a dose indicating mechanism comprising a first spool and a second spool. First and second spools are rotatably supported in the housing. Additionally, first and second spools are oriented substantially parallel to each other and substantially parallel to the piston rod. Typically, first and second spools are separated in radial direction and may be arranged at the same or at least in overlapping axial portions of the housing.

The dose indicating mechanism and hence the drive mechanism further comprises a dose indicating tape or a dose indicating belt coiled onto at least the second spool and fixed with another end to an outer circumference of the first spool. The dose indicating tape therefore extends between the first and second spools and can be selectively and alternately coiled onto first and second spools.

Typically, during a dose setting procedure the first spool is rotatable to unroll or to unwind the dose indicating tape from the second spool at the benefit of coiling up the dose indicating tape to the first spool. The dose indicating tape typically comprises a series of numbers or other indicia in order to visually display the size of a dose to a user through a dose indicating window provided in the surrounding housing of the drive mechanism. Hence, the dose indicating mechanism is arranged inside the housing of the drive mechanism in such a way, that the dose indicating tape extending between first and second spools at least partially shows up below the dose indicating window of the housing.

Since the dose indicating tape is operable to be coiled up onto first and second spools, respectively, the overall length of the tape can be rather large in order to provide almost unlimited space for printing numbers of other indicia thereon. The respective indicia or numbers presented on the dose indicating tape may therefore be comparatively large therefore providing a good visibility and allowing for a sufficient and unequivocal reading thereof, even by patients or users suffering impaired vision.

The arrangement of first and second spools to coil up or to unwind a dose indicating tape is rather space saving yet providing comparatively large numbers or indicia.

Radial separation of first and second spools is of particular benefit in order to provide the numbers printed thereon in a region between the two spools in which the dose indicating tape is at least partially rather flat or even-shaped, thereby allowing to present the numbers or indicia of the dose indicating tape in a rather unadulterated way.

In a further embodiment, the second spool is rotatable in a dose incrementing direction against the action of a spring, typically embodied and denoted as spool spring. The spool spring is either indirectly or directly coupled to the rotatably supported second spool in order to keep the spool in an initial configuration, in which a major portion of the dose indicating tape is wound up on the second spool.

Moreover, in the initial configuration another free end of the dose indicating tape may be just connected to the outer circumference of the first spool. Additionally, it is also conceivable, that a limited number of layers of the dose indicating tape is coiled up on the first spool. A driving force for rotating first and second spools simultaneously is typically provided to the first spool. Then, by means of a rotation of the first spool and by the interconnection of first and second spools via the dose indicating mechanism also the second spool will start to rotate against the action of the spool spring.

For a reverse motion and for setting the dose indicating mechanism into an initial configuration the second spool may rotate under the action of the spool spring in a dose decrementing direction, thereby also inducing a respective dose decrementing rotation of the first spool by means of the dose indicating tape. Hence, the spool spring is operable to exert a restoring force and to induce a restoring action on the dose indicating mechanism, e.g. during a dose dispensing procedure.

Typically, the numbers or indicia printed on the dose indicating tape will show up in an increasing order when first and second spools are rotated in a dose incrementing way, in particular during dose setting. During dose dispensing, the numbers of the dose indicating tape will show up in the dose indicating window in reverse order. Hence, respective numbers will count down.

According to another embodiment, the first spool is rotatably engaged with a drive sleeve of the drive mechanism which is operable to set a dose. Typically, the drive sleeve is operably engaged with a dose setting member during a dose setting procedure. Moreover, during dose setting the drive sleeve is typically disengaged from the piston rod.

It is only during dose dispensing, that the drive sleeve is disconnected or disengaged from a dose setting member while it is mechanically engaged with the piston rod, either directly or indirectly for driving the same in distal direction for dispensing of a dose. The drive sleeve is typically oriented parallel to the piston rod. The hollow drive sleeve may further be adapted to receive the piston rod therein. Even though the piston rod may be located inside the drive sleeve, piston rod and drive sleeve may be arranged in a substantially contactless way. Hence, a rotation of the drive sleeve during dose dispensing may be transferred via further functional components of the drive mechanism to the piston rod.

In a further embodiment, the drive sleeve is axially fixed relative to the housing of the drive mechanism. It is then due to at least one clutch member, preferably displaceable in axial direction between a proximal and a distal stop, that the drive sleeve is operably engageable and disengageable with regard to the piston rod for dispensing and for setting of a dose, respectively.

In a further embodiment, the first spool comprises a gear wheel directly or indirectly engaged with a gear wheel of the drive sleeve. Accordingly, the first spool is arranged radially offset from the drive sleeve. By means of mutually engaging gear wheels of the first spool and the drive sleeve, a rotation of the drive sleeve can be permanently transferred to the first spool and hence to the dose indicating mechanism. Typically, the drive sleeve is operable to rotate in a dose incrementing direction during setting of a dose and in a reverse, dose decrementing direction during dispensing of a dose.

Since the first spool of the dose indicating mechanism is permanently engaged with the drive sleeve, the configuration of the dose indicating mechanism, hence the configuration of its dose indicating tape is inherently indicative of the number of turns of the drive sleeve.

In a further embodiment, the first and second spools are located on opposite lateral sides of the drive sleeve. Hence, first and second spools are both radially offset from each other as well as radially offset from the drive sleeve. Preferably, first and second spools may be arranged on diametrically opposite sides of the drive sleeve. It is generally conceivable, that the center of first and second spools are intersected by a virtual, radially extending line overlapping also with the centre or the axis of rotation of the drive sleeve.

In alternative embodiments it is also conceivable, that the axis of rotation of first and second spools and the drive sleeve are arranged to form a virtual triangle. Here, the first and second spools are not located diametrically opposite the drive sleeve but a virtual line as seen in a radial cross-section connecting the spools' axes of rotation may extend at an angle of larger than 15°, 30°, 45°, or even larger 60° with respect to a virtual interconnecting line between the drive sleeve and any one of the spool axes.

Irrespective of the relative arrangement of first and second spools and the drive sleeve the dose indicating tape extending between the first and second spools effectively extends across the drive sleeve. Typically, the dose indicating tape extending between first and second spools at least radially overlaps with the drive sleeve but remains out of contact with regard to the drive sleeve. In particular, the drive sleeve may be arranged midway between first and second spools. In this way, a rather symmetric arrangement of first and second spools relative to the drive sleeve can be obtained.

Since the first and second spools may be located radially offset and radially outwardly from the tubular shaped drive sleeve, the outer housing of the drive mechanism may require and may comprise at least one respective radially outwardly bulged portion to accommodate first and second spools, respectively.

According to another embodiment, the dose indicating tape extends across a support located between the first and the second spool. Here, the support radially supports the dose indicating tape with respect to the orientation of the drive sleeve located underneath. The support may provide a gliding surface in order to provide a smooth and frictionless gliding of the dose indicating tape across the support. Moreover, the support may also provide an axial guiding function in order to prevent, that the dose indicating tape becomes subject to axial displacement or axial offset when unwound or coiled up from or to first and second spools, respectively.

By means of the support the dose indicating tape can be supported below the dose indicating window in order to prevent that the dose indicating tape sags between the two spools. Moreover, and by means of the spool spring, the dose indicating tape extending between first and second spools is always strained and substantially free of slack in order to provide a good and sufficient visibility of its numbers or indicia.

According to another embodiment at least one of first and second spools comprises a bearing portion axially offset from the dose indicating tape and rotatably arranged in an axially extending bearing recess of the housing. The portion of the first and second spools to engage with the dose indicating tape may serve as a bobbin and may therefore be denoted as a bobbin portion of first and second spools, respectively. The bearing portion and the bobbin portion may be integrally formed. The bearing portion may either comprise a hollow receptacle to receive an axially extending pin of the housing.

Moreover, it is conceivable, that the bearing portion of first and/or second spools is radially and circumferentially confined in the axially extending bearing recess of the housing. In this way, the bearing portion of first and/or second spools may be reduced in diameter and radial dimensions compared to respective bobbin portions. Additionally, by providing at least one axially extending bearing recess, the assembly of first and/or second spools in the housing of the drive mechanism may be straight forward. Typically, the bearing recesses of the housing feature a distal stop face in order to provide not only a rotatable but also an axial support for the first and/or second spool of the dose indicating mechanism.

According to a further embodiment, the gear wheel is located at a distal offset from the dose indicating tape. Typically, the gear wheel may be located axially between the bearing portion and the bobbin portion of the first spool. In this way, a torque to set the first spool in rotation can be exerted to an axial center region of the first spool; thereby limiting an eventual torque induced radial displacement or radial slack of the first spool.

Furthermore, the gear wheel of the first spool is arranged axially adjacent to the bearing portion in order to transfer a rotation inducing torque in a rather unadulterated way to the respective spool.

According to another embodiment, the spool spring comprises a helical spring engaged with the housing and with the second spool with opposite end sections. The spool spring may either be directly engaged with the bobbin portion of the spool or with the axially offset bearing portion thereof. Apart from a helical spring arrangement it is also conceivable, that the spool spring comprises a spiral or coil spring which may equally serve to directly store rotational energy corresponding to a rotational movement of the first spool or drive sleeve, respectively.

According to another embodiment the spool spring is located radially between the bearing portion of the second spool and the bearing recess of the housing. Hence, the helically shaped spool spring is radially sandwiched between the bearing portion of the second spool and the enclosing bearing recess of the housing. In this embodiment the bearing recess of the housing also provides a well-defined mount for the helical spring. In order to mechanically engage one end of the spool spring with the bearing recess of the housing it may be of further benefit, when the bearing recess only partially encloses the bearing portion of the second spool.

In order to provide a completely surrounding bearing recess the housing of the drive mechanism may further comprise multiple components that compliment each other to form a bearing recess to accurately and precisely receive the bearing portion of the second spool.

Moreover, and according to another embodiment, at least one of first and second spools is axially constrained by the bearing recess and a proximal closure of the housing. While the bearing recess may for instance provide a distal axial stop for the first and/or second spool, the proximal closure of the housing may provide an oppositely located, hence proximal stop, by way of which first and/or second spools can be axially fixed relative to the housing.

In an alternative embodiment it is also conceivable, that first and second bearing portions of first and second spools are located proximally offset from the bobbin portion and hence from the dose indicating tape. In this configuration a proximal closure of the housing may serve as an axial stop for the spools' bearing portions.

It is generally intended, that first and second spools with their bobbin portion and bearing portion are arranged at approximately the same axial position. However, and according to another embodiment it is also conceivable, that only the bobbin portions of first and second spools radially overlap while respective first and second bearing portions thereof extending in opposite axial directions.

According to another embodiment, the spool spring may not be arranged axially offset from the bobbin portion of the second spool but may be located inside the second spool. In this embodiment, the second spool may consist of a bobbin portion operable to coil up the dose indicating tape. Here, it is required, that the second spool is substantially hollow to receive at least the spool spring therein. Hence, one end of the spool spring may operably engage with an inside facing portion of the hollow second spool while another and opposite end portion of the spool spring may be engaged and connected to a housing portion, e.g. to a bearing of the housing at least partially extending into the hollow spool in axial direction in order to rotatably support the same.

According to another embodiment, first and the second spools are rotatably supported on a common insert or base which is fixable in the housing of the drive mechanism and/or in the housing of the drug delivery device. Preferably, said common insert or base is axially and rotatably fixable in said housing. The insert or base is further operable to provide a preassembly of the dose indicating mechanism.

In particular, it may be the insert which provides at least one bearing recess or a respective bearing portion to rotatably engage with at least one of first and second spools. In this way, the dose indicating mechanism may be preassembled on the basis of the insert. Hence, first and second spools together with the interconnecting dose indicating tape may be assembled to and with the common insert to form a dose indicating preassembly. In a subsequent step of assembly, the preassembled dose indicating mechanism may be inserted into the housing. The overall assembly of the drive mechanism may therefore be modularised in order to provide an efficient, fast and reliable assembly of the drive mechanism.

According to another aspect, the invention also relates to a drug delivery device for dispensing of a dose of a medicament. The drug delivery device comprises a drive mechanism as described above and a cartridge at least partially filled with the medicament to be dispensed by the drug delivery device. The cartridge is arranged in the housing of the drive mechanism or in a cartridge holder of the drug delivery device which is fixed to the housing either releasably or non-releasably, e.g. in case of a disposable drug delivery device. Consequently, the drug delivery device comprises a cartridge holder to receive and to accommodate a cartridge filled with the medicament.

In case of a disposable drug delivery device the cartridge is not to be replaced when empty but the entire device is intended to be discarded. With a reusable device, the drive mechanism can be reset and an empty cartridge can be generally replaced by a new one.

Apart from that, the drug delivery device and the drive mechanism may comprise further functional components, such like an injection button, by way of which a user may trigger and control the drug delivery device and its drive mechanism for dispensing of a dose of the medicament.

In the present context, the distal direction points in the direction of the dispensing and of the device, where a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

Generally, by means of the spring element operably engaged with the drive member, a semi-automated drug delivery device can be provided. During a dose setting procedure the spring element can be strained or tensioned to such a degree, that a dose dispensing action of the drug delivery device can be exclusively driven by the relaxing action of the biased spring element. Hence, dose dispensing is completely governed by the action of a spring element previously tensioned and strained in a dose setting procedure.

The drive mechanism particularly serves to displace a piston rod in axial direction for the purpose of dispensing of a dose of a medicament. In addition, the drive mechanism typically comprises components which also form part of and have a function in at least one of the following mechanisms: a dose setting mechanism, a last dose limiting mechanism and a dose indicating mechanism. As will be apparent from the embodiments described herein, various components of e.g. the drive mechanism also belong to at least one of the dose setting mechanism, the last dose limiting mechanism and/or to the dose indicating mechanism; and vice versa. Hence, the invention as described herein equally refers to and defines a drive mechanism, a dose setting mechanism, a last dose limiting mechanism and/or a dose indicating mechanism of a drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(02)25, Asp28] Exendin-4(1-39)-NH2,
des Pro36, Pro37, Pro38 [Met(0)14, Trp(O2)25, Asp28] Exendin-4(1-39)-(Lys)6-NH2,
H-(Lys)6-des Pro36, Pro37, Pro38 [Met(O)14, Trp(02)25, Asp28] Exendin-4(S1-39)-(Lys)6-NH2,
H-Asn-(Glu)5-des Pro36, Pro37, Pro38 [Met(O)14, Trp(02)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, an embodiment of the invention will be described by making reference to the drawings, in which:

FIG. 24 is a perspective view of the dose limiting member at the beginning of a dose incrementing displacement, FIG. 24a shows the clicking member of the dose limiting member according to FIG. 24, FIG. 25 shows the dose limiting member during a dose decrementing displacement, FIG. 25a shows an enlarged view of the clicking member of the dose limiting member according to FIG. 25.

DETAILED DESCRIPTION

Figure 1:
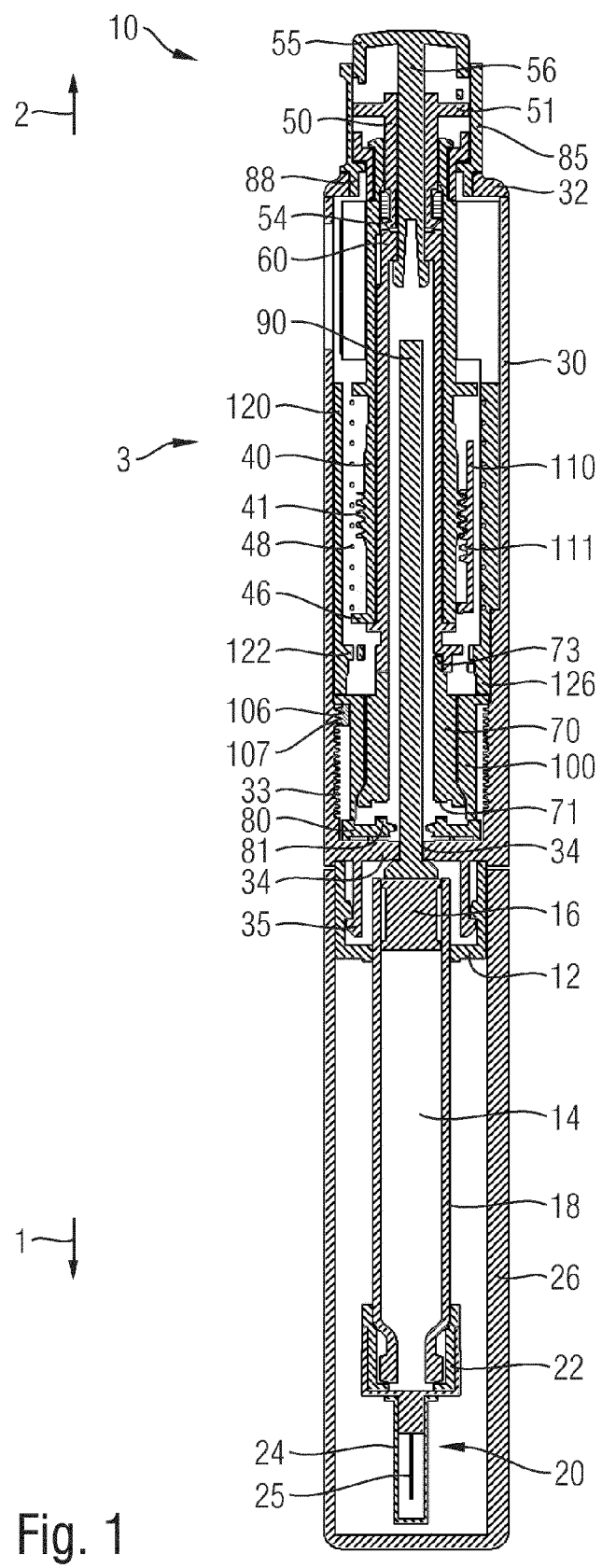
FIG. 1 schematically illustrates a drug delivery device in longitudinal cross-section.
Figure 2:
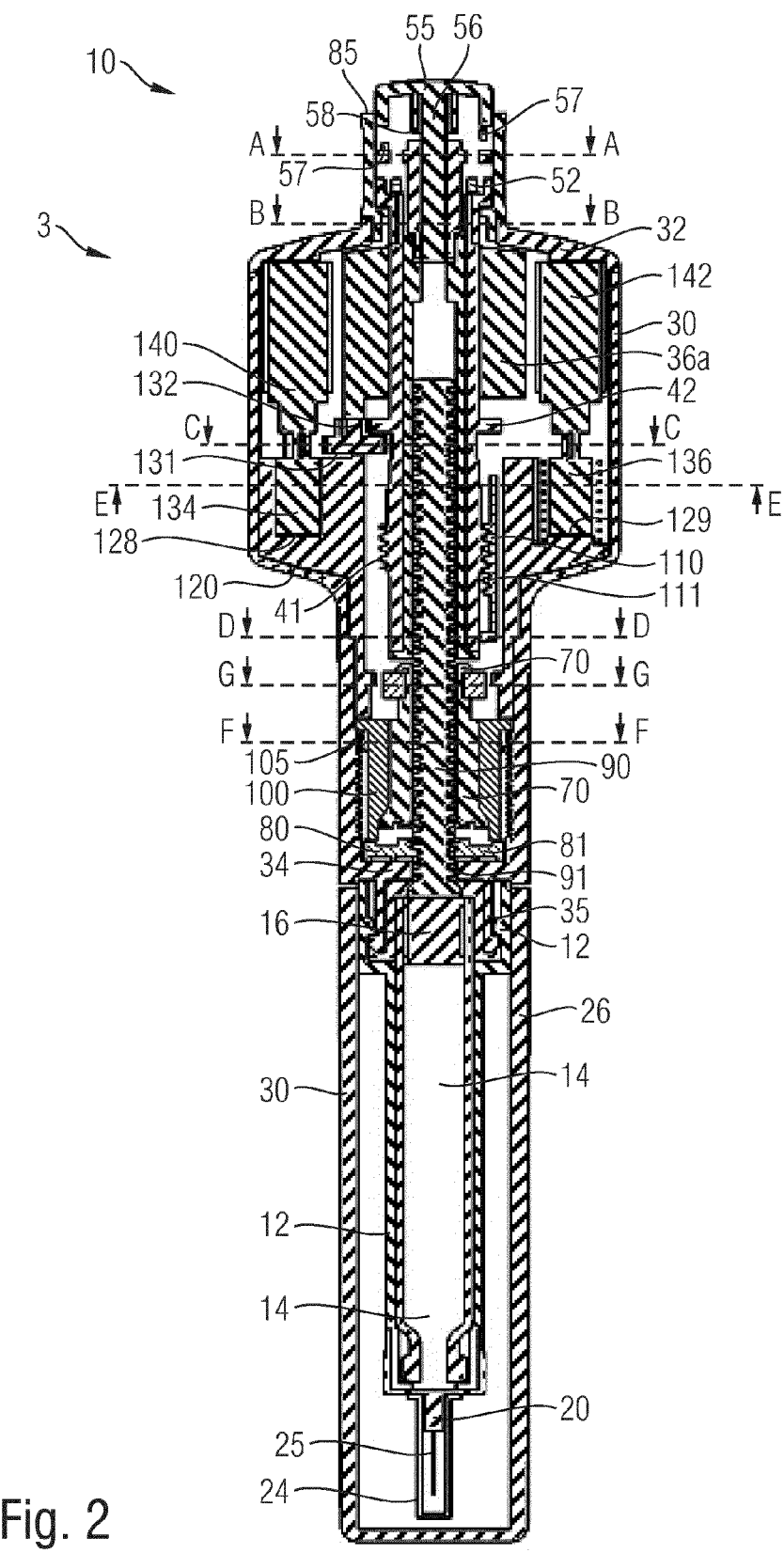
FIG. 2 shows another longitudinal cross-section of the drug delivery device rotated about 90° around its longitudinal axis.
Figure 10:
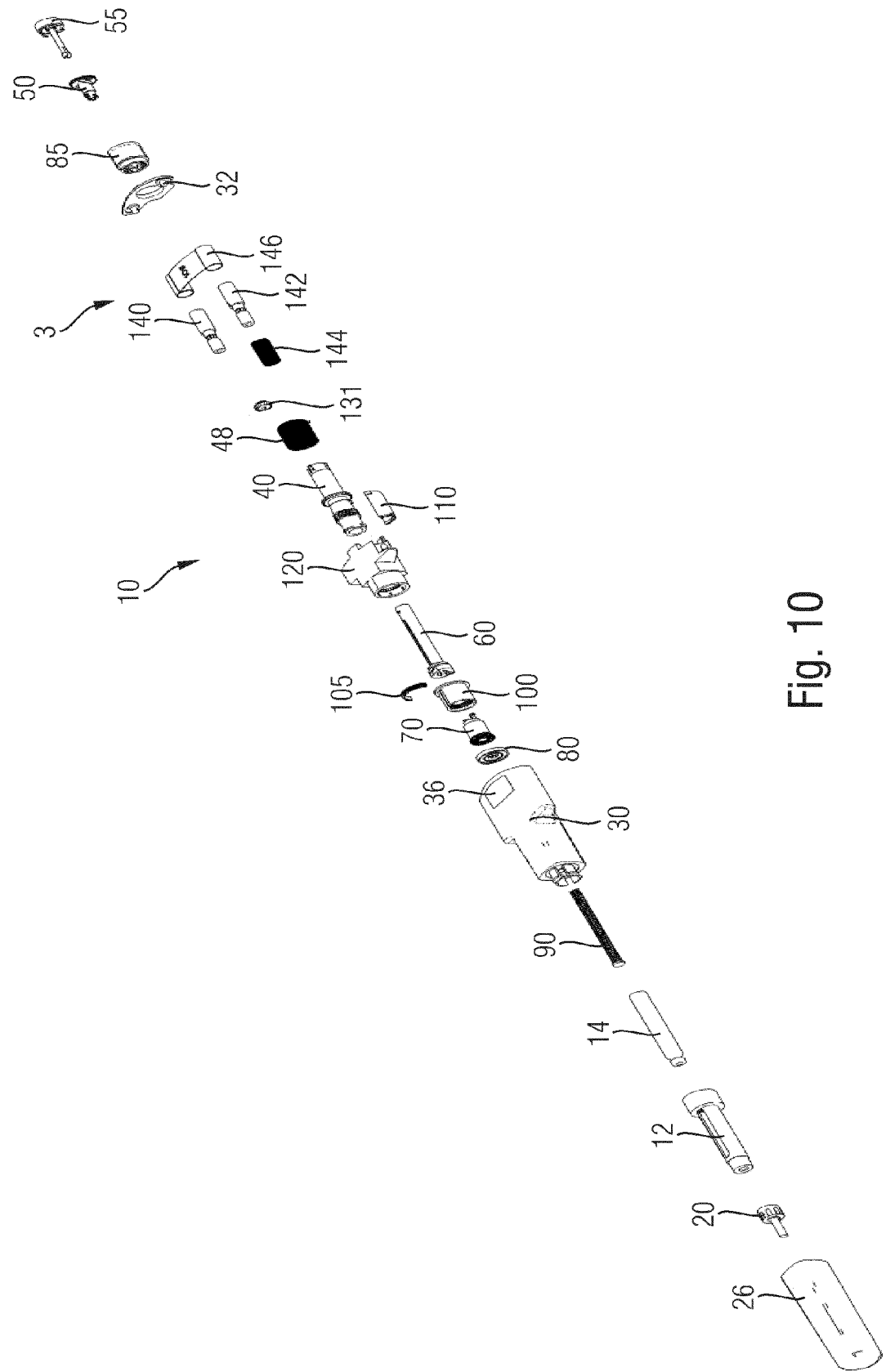
FIG. 10 shows an exploded view of the drug delivery device in perspective illustration.
Figure 11:
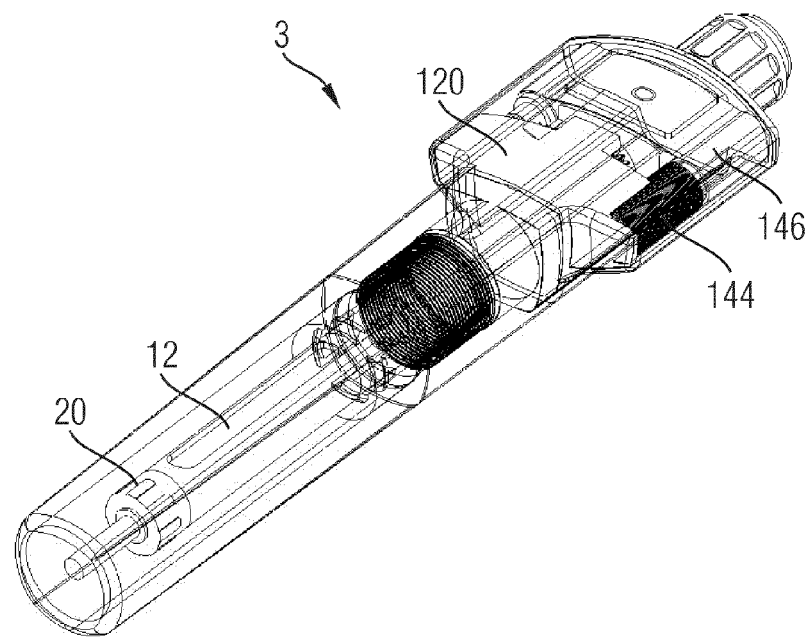
FIG. 11 shows a partially transparent view through the assembled drug delivery device.

In FIGS. 1, 2 and 10 the drive mechanism 3 of the drug delivery device 10 is illustrated in an assembled and in an exploded view, respectively. The drug delivery device 10 may be of pen-injector type and may comprise a substantially cylindrical and axially elongated shape. In the present set of Figures, the axial direction is denoted with reference number 1 and the opposite proximal direction is indicated by reference number 2. The drug delivery device 10 comprises a proximal housing component 30 to receive and to accommodate the drive mechanism 3 and in particular the functional and moveable components, the drive mechanism 3 is made of.

In distal direction 1, the housing 30 is connected with a cartridge holder 12 which is adapted to accommodate and to receive a cartridge 14 containing the medicament to be dispensed by the drug delivery device 10. The cartridge 14 typically comprises a vitreous barrel 18 of cylindrical shape which is sealed in distal direction 1 by a pierceable sealing member, such like a septum.

In proximal direction 2, the cartridge 14 is sealed by a piston 16 slidably arranged in the vitreous barrel 18 of the cartridge 14. Displacement of the piston 16 in distal direction 1 leads to a respective built-up of a fluid pressure inside the cartridge 14. When the distal outlet of a cartridge 14 is connected with e.g. a needle assembly 20, as shown in FIG. 1, a predefined amount of the liquid medicament contained in the cartridge 14 can be expelled and dispensed via an injection needle 25 of the needle assembly 22.

In FIG. 2 however, a needle cap 24 to protect the double-tipped injection needle 25 is indicated. The needle assembly 20 is typically arranged on a distal end portion of the cartridge holder 12. Typically, a distally located socket of the cartridge holder 12 and a needle hub 22 of the needle assembly 20 comprise mutually corresponding threads to screw the needle assembly 20 onto the cartridge holder 12 in a releasable and removable way.

The cartridge holder 12 and hence the cartridge 14 is to be protected and covered by a protective cap 26 which is shown in FIGS. 1 and 2. Prior to setting and/or dispensing of a dose, the protective cap 26 as well as the inner needle cap 24 are to be removed. After dispensing or injecting of the medicament into biological tissue, the needle assembly 20 is typically to be discarded and the distal end of the drug delivery device 10 is to be covered by the protective cap 26.

The drive mechanism 3 as illustrated in an exploded view in FIG. 10 and as shown in cross section in its fully assembled configuration in FIGS. 1 and 2 comprises numerous functional components by way of which a dose of variable size can be set and subsequently dispensed.

The dose dispensing procedure comes along with a distally directed advancing displacement of the piston rod 90 relative to the housing 30. The drive mechanism 3 therefore comprises at least a housing 30, a piston rod 90, a drive wheel 80 or drive nut and a drive sleeve 40 which can be selectively and operably coupled for setting and dispensing of a dose, respectively.

The dose dispensing procedure comes along with a distally-directed advancing displacement of the piston rod 90 relative to the housing 30. As illustrated for instance in FIG. 2, the piston rod 90 comprises an outer thread 91 which is typically rotatably locked to a radially inwardly extending support 34 of the housing 30. Advancing of the piston rod 90 in distal direction relative to the housing 30 is typically achieved by a rotation of the drive wheel 80 threadedly engaged with the piston rod 90 and being axially fixed in the housing 30.

In the following, setting of a dose is described.

For setting of a dose, a user typically takes the drug delivery device 10 and starts to rotate the proximally located dose setting member 85 relative to the proximal housing 30. Here, the dose setting member 85 comprises a dose dial, which is axially fixed to the housing 30 and which may be arbitrarily dialled either clockwise or counter-clockwise for incrementing and decrementing a dose to be set accordingly.

Figure 3:
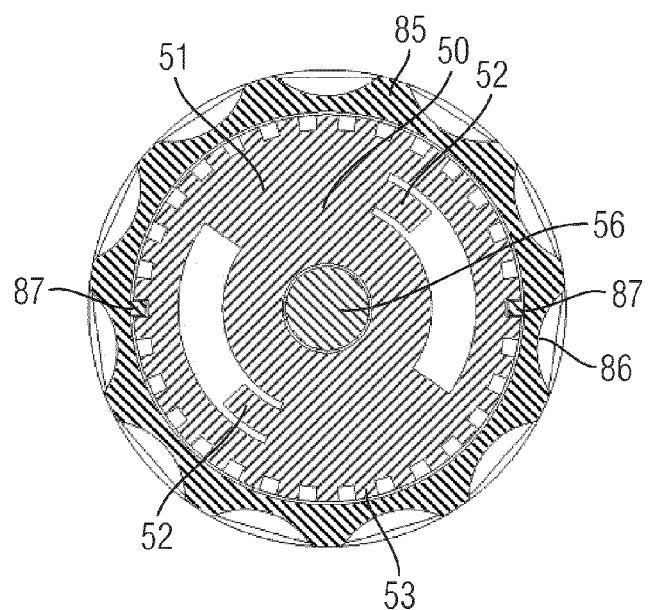
FIG. 3 shows a cross-section along A-A according to FIG. 2.

As in particular illustrated in FIG. 3, the dose setting member 85 comprises a rippled structure 86 at its outer circumference, which allows and supports a slip-free gripping and dialling thereof. Moreover, the dose setting member 85 has the form of a hollow sleeve and features two diametrically oppositely located and radially inwardly extending protrusions 87 engaging with a toothed geared rim 53 of a proximal clutch member 50 being rotatably supported in the housing 30.

As further illustrated in FIGS. 1 and 2, the housing 30 comprises a proximal closure or lid 32 which is axially intersected by the dose setting member 85, by the proximal clutch member 50 and by a dose dispensing button 55 proximally protruding from the dose setting member 85. As further indicated in FIGS. 1, 2 and in FIGS. 20, 21, the dose setting member 85 comprises a distally extending projection 88 of rim or ring-like shape extending into or through the proximal closure 32 of the housing 30. By means of the projection 88, the dose setting member 85 may be axially fixed to the housing 30.

The proximal clutch member 50 comprises an axially extending shaft portion 56 to axially and rotatably engage with a main clutch member 60 featuring a sleeve-like geometry. The proximal clutch member 50 typically comprises a fastening or fixing element 54 at its distal end of its shaft portion 56 to rotatably and to axially engage with the main clutch member 60. In this way, a rotation of the proximal clutch member 50 typically induced by dialling of the dose setting member 85 can be equally and directly transferred into a respective rotation of the main clutch member 60.

Figure 5:
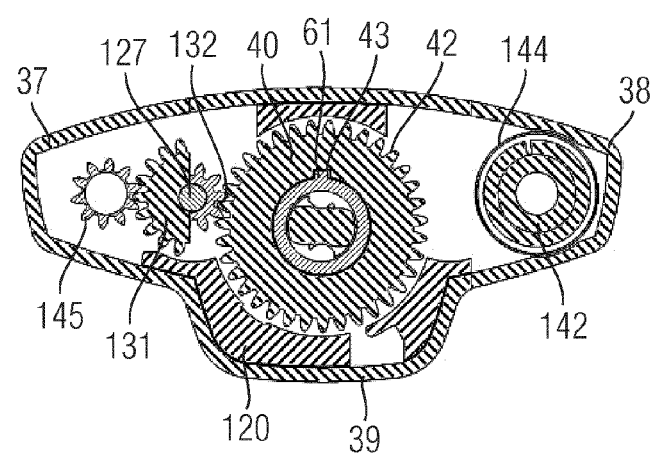
FIG. 5 shows a cross-section along C-C according to FIG. 2.
Figure 6:
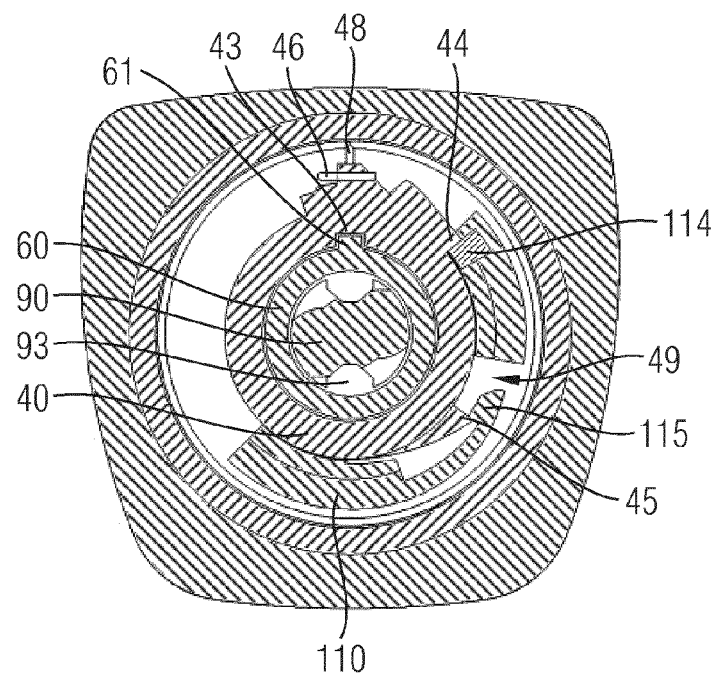
FIG. 6 shows a cross-section along D-D according to FIG. 2.

The main clutch member 60 is rotatably engaged with the drive sleeve 40 adapted to accommodate both, a distal end of the proximal clutch member 50 and almost the entirety of the main clutch member 60 extending almost all the way through the drive sleeve 40 in distal direction 1. As shown in FIGS. 5 and 6, the main clutch member 60 comprises a radially outwardly and axially extending ridge or protrusion 61 serving as a fastening element to rotatably engage with a correspondingly shaped groove or notch 43 provided at an inside facing portion of the drive sleeve 40.

By means of the radially outwardly extending protrusion 61 of the main clutch member 60 and the correspondingly shaped groove 43 of the drive sleeve 40, a splined engagement of main clutch member 60 and drive sleeve 40 can be provided. Consequently, the drive sleeve 40 and the main clutch member 60 are rotatably locked but the main clutch member 60 is free to be displaced in axial direction 1, 2 relative to the drive sleeve 40.

Figure 12:
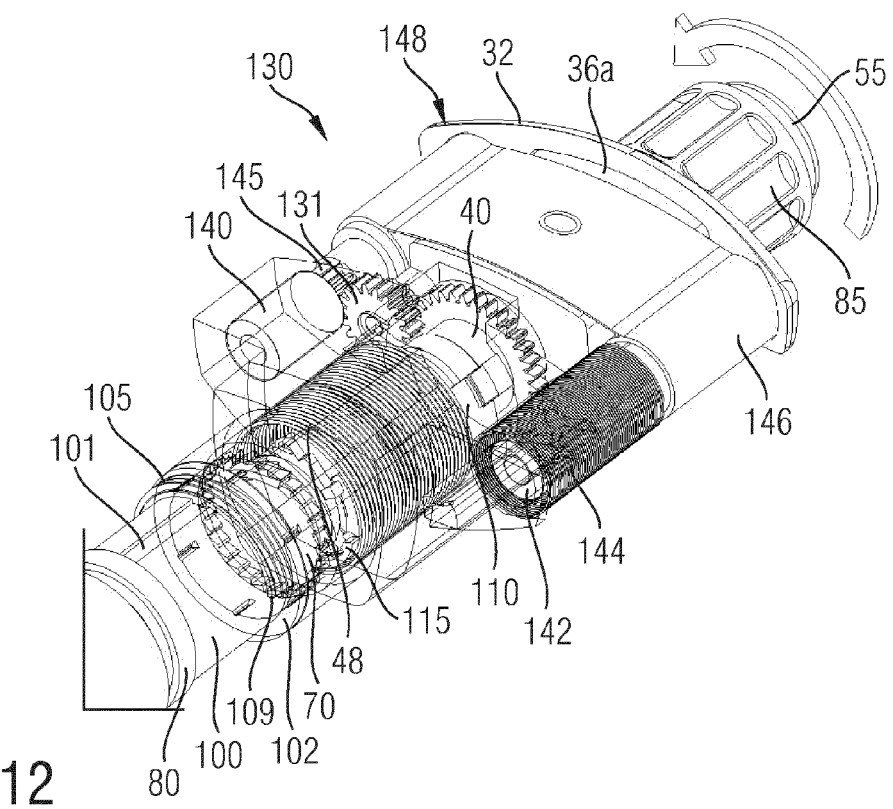
FIG. 12 is a perspective view of the dose indicating mechanism.

As illustrated in FIGS. 6 and 12 the drive sleeve 40 is connected with one end of a helical spring 48 extending around and enclosing the distal portion of the drive sleeve 40. The opposite end of the spring 48 is connected to an insert 120 which is fixedly connected to the housing 30. In this way, the drive sleeve 40 is rotatable in a dose incrementing direction 4 against the action of the helical spring 48.

Figure 9:
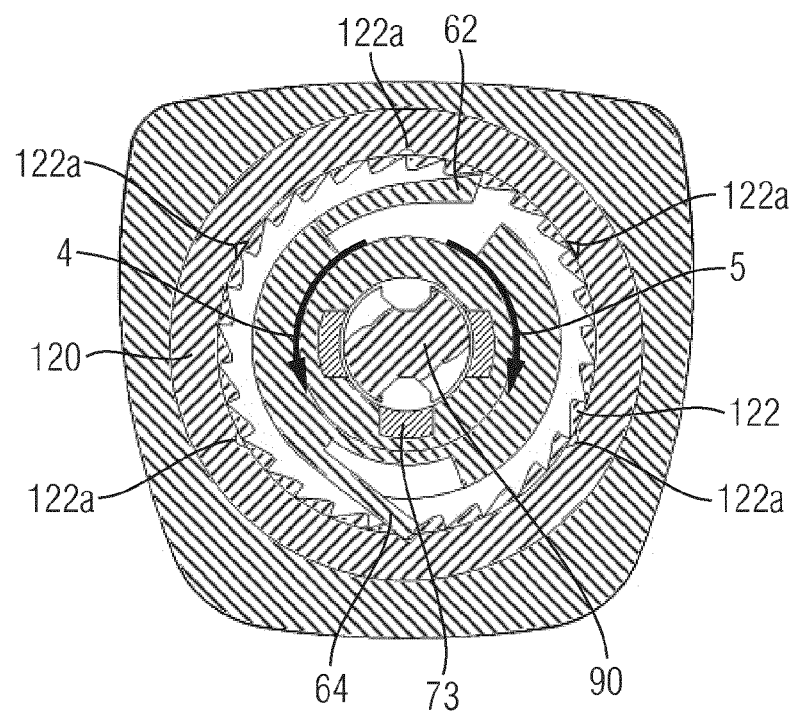
FIG. 9 shows a cross-section along G-G according to FIG. 2.

As further shown in FIG. 9 a pawl-like and radially outwardly extending ratchet member 62 is adapted to engage with a toothed ring portion 122 of the insert 120. The toothed ring 122 comprises a saw tooth profile such that the radially outwardly biased ratchet member 62 of the main clutch member 60 consecutively and stepwise engages with the toothed ring 122 in order to store and save mechanical energy of the strained helical spring 48 during a dose setting procedure. Here, the main clutch member 60 and the drive sleeve 40 rotatably locked therewith can be rotated in a dose incrementing direction 4 in discrete steps, e.g. corresponding to an international unit in case of a drug delivery device adapted for administering of insulin.

The engagement of the ratchet member 62 and the toothed ring 122 is such, that also a dose decrementing rotation 5 is possible when a respective torque is applied to the dose setting member 85 and hence to the main clutch member 60. The toothed flanks of the ratchet member 62 and the teeth of the toothed ring 122 are designed such, that also a well-defined and precise dose decrementing rotation of the main clutch member 60 and hence of the drive sleeve 40 is possible, in particular for correcting and for decrementing a dose that would be too large otherwise.

Figure 13:
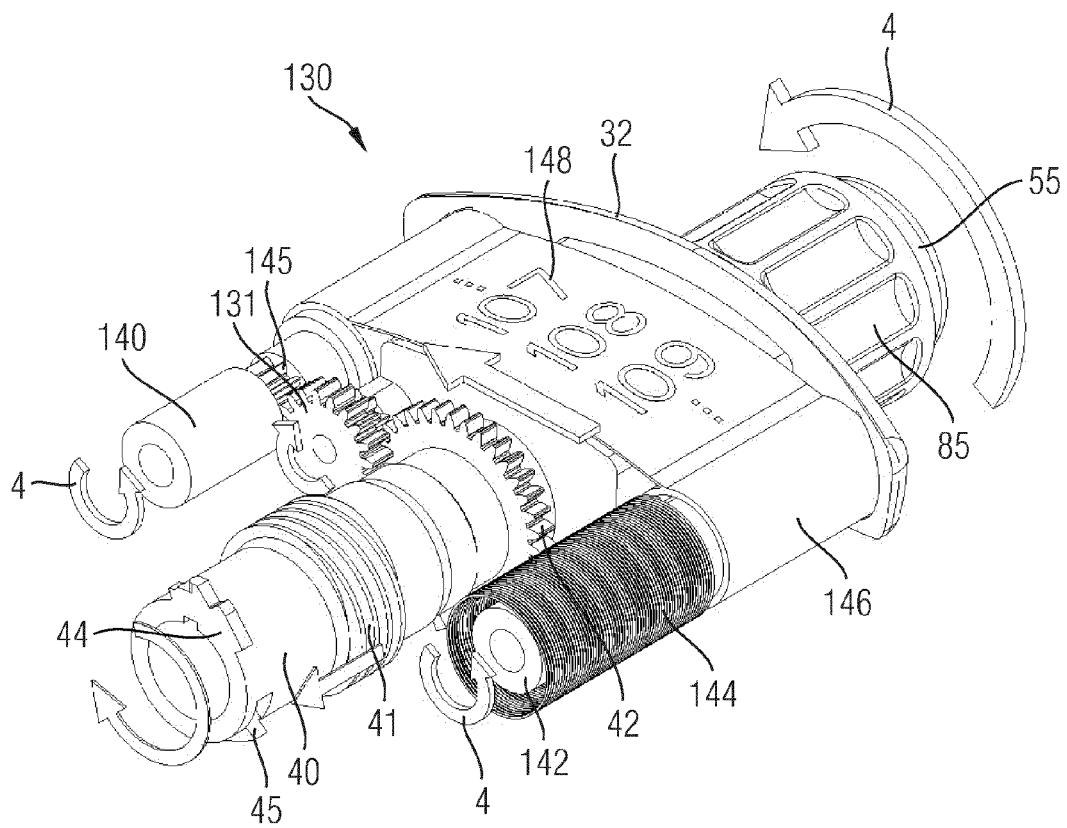
FIG. 13 shows an isolated view of the dose indicating mechanism.

As for instance illustrated in FIGS. 6, 7 and 12, 14 and 15 there is also provided a dose limiting member 110 acting as a single dose limiting member during a dose setting procedure. The dose limiting member 110 is threadedly engaged with the drive sleeve 40. As illustrated in FIG. 13, the drive sleeve 40 comprises only a limited axial portion provided with an outer thread 41. Said outer thread 41 is located offset from a distal end as well as from a proximal end of the drive sleeve 40. Adjacent to the threaded portion 41, the outer circumference of the drive sleeve 40 is rather smooth shaped.

Figure 7:
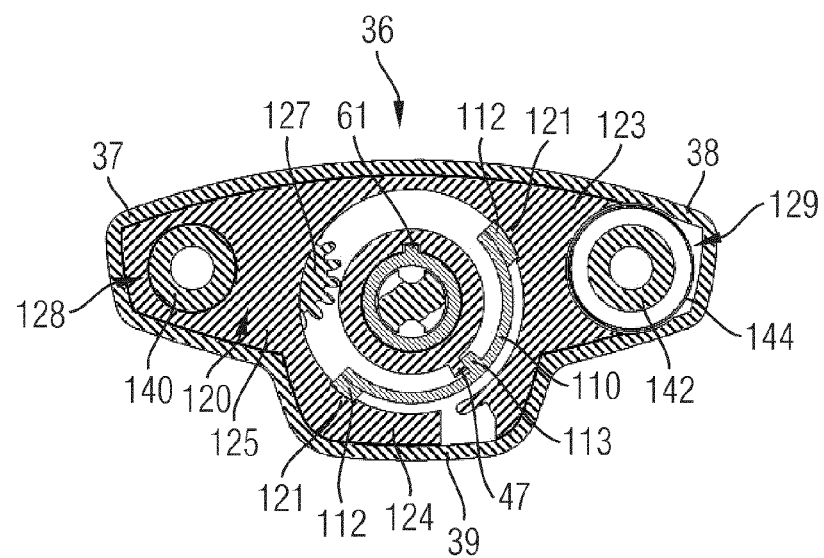
FIG. 7 shows a cross-section along E-E according to FIG. 2.

As shown in FIGS. 6 and 7, the dose limiting member 110 is of shell-like shape and extends only partially around the outer circumference of the drive sleeve 40. As further illustrated in FIG. 6, a distal end of the dose limiting member 110 extends radially between the drive sleeve 40 and the helical spring 48. Moreover, the distal end of the drive sleeve 40 comprises a radially outwardly extending spring mount 46 to engage with the distal end of the helical spring 48.

Figure 14:
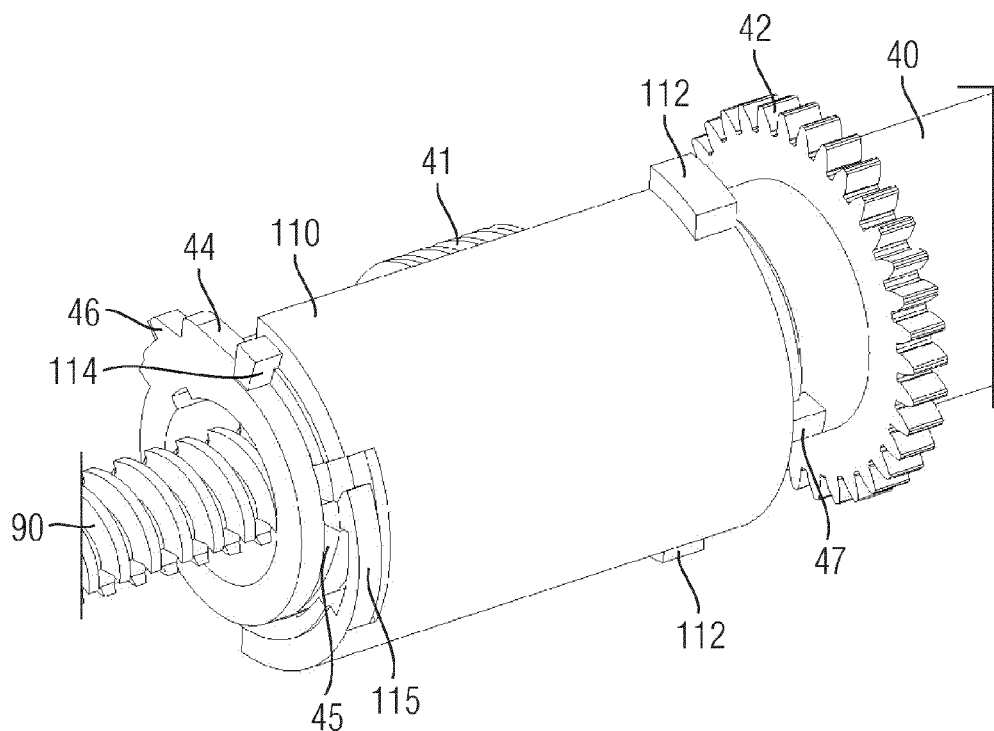
FIG. 14 shows the dose limiting member in a zero dose configuration on the drive sleeve.
Figure 15:
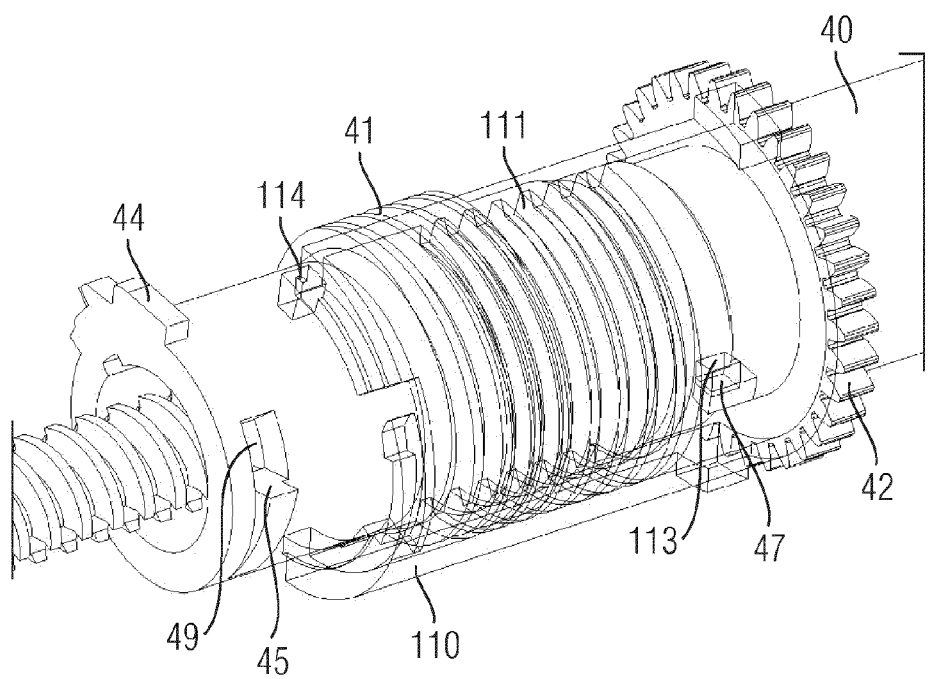
FIG. 15 shows the dose limiting member according to FIG. 14 in a maximum dose configuration.
Figure 16:
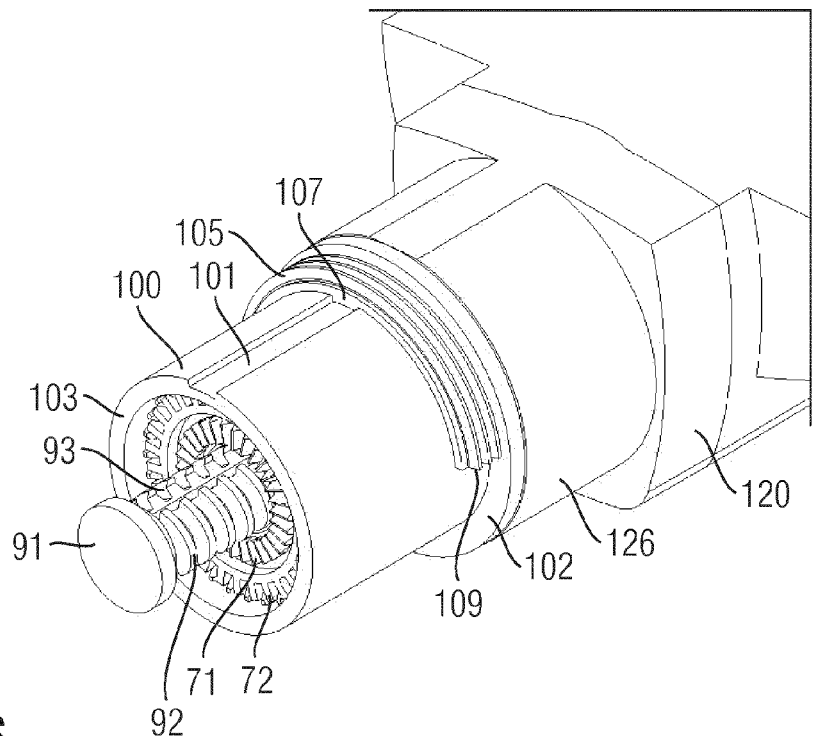
FIG. 16 shows a perspective view of a last dose limiting mechanism.

According to FIG. 15, the dose limiting member 110 comprises an inner thread 111 to engage with the outer threaded portion 41 of the drive sleeve 40. As further illustrated in FIGS. 7 and 14 the dose limiting member 110 comprises two diametrically oppositely located radially outwardly extending protrusions 112 engaging with correspondingly formed recesses 121 of the insert 120.

The cross-section according to FIG. 7 further illustrates that the insert 120 almost entirely fills the interior volume of the surrounding housing 30. Therefore, the insert 120 is fixedly connected to the housing 30 and serves as a housing portion to provide a mounting base for various functional components of the drive mechanism 3.

By means of mutually engaging protrusions 112 and grooves 121 the dose limiting member 110 is rotatably locked to the insert 120 and hence to the housing 30. Moreover, since the dose limiting member 110 is also threadedly engaged with the drive sleeve 40, a rotation of the drive sleeve 40 in dose incrementing direction 4, as illustrated in FIG. 24 leads to a proximally directed displacement of the dose limiting member 110. An oppositely directed rotation of the drive sleeve 40 in dose decrementing direction 5 leads to a respective opposite, hence distally directed displacement of the dose limiting member 110 relative to the insert 120, the housing 30 and relative to the drive sleeve 40 as illustrated in FIG. 25.

Moreover, FIGS. 7, 12, 14 and 15 show that the dose limiting member 110 comprises a radially inwardly extending first stop 113 near its proximal end which is adapted to circumferentially abut with a correspondingly shaped but radially outwardly extending first stop 47 of the drive sleeve 40. The configuration as indicated in FIGS. 7 and 15 may relate to a maximum dose configuration, in which the mutual abutment of first stops 47, 113 of drive sleeve 40 and dose limiting member 110 inhibits a further rotational displacement of the drive sleeve 40 in dose incrementing direction 4. In this way, a maximum dose for a single dose dispensing procedure can be effectively limited.

Later on and during dose dispensing or during dose correction, i.e. when the drive sleeve 40 is rotated in a dose decrementing direction 5, the dose limiting member 110 will be displaced in distal direction 1 in order to return into its initial zero dose configuration as it is indicated for instance in FIG. 14. Also here, mutually corresponding second stops 44, 114 of drive sleeve 40 and dose limiting member 110 are provided. While the second stop 44 of the drive sleeve 40 extends radially outwardly from a distally located rim of the drive sleeve 40 the second stop 114 of the dose limiting member 110 is located at a distal and circumferential edge of the shell-shaped dose limiting member 110. In particular, the second stop 114 is provided at a leading edge with respect to a rotation in dose decrementing direction 5.

In contrast to that, the first and radially inwardly extending stop 113 of the dose limiting member 110 extends substantially midway between the diametrically oppositely located radially outwardly extending protrusions 112. Moreover, the protrusions 112 and the first stop 113 are located in a common transverse plane as indicated in FIG. 7. In this way, forces or torque introduced into the dose limiting member 110 via the rotating drive sleeve 40 can be smoothly and directly transferred to the insert 120.

Since the dose limiting member 110 almost completely extends through the helical spring 48 in axial direction a rather compact and space saving arrangement for the dose limiting member 110 can be attained.

As further illustrated for instance in FIG. 12 the drive mechanism 3 also comprises a dose indicating mechanism 130 featuring first and second spools 140, 142 rotatably supported in the housing 30 and being oriented substantially parallel to each other as well as being oriented substantially parallel to the drive sleeve 40 and the piston rod 90 extending therethrough. The two spools 140, 142 are further mutually connected by means of a dose indicating tape 146 having several numbers 148 printed thereon.

As shown in FIGS. 2 and 12 the first spool 140 is rotatably engaged with the drive sleeve 40 by means of a series of gear wheels 42, 131. Here, the drive sleeve 40 comprises a gear wheel 42 that mates with a sprocket 132 of a gear wheel 131. Said gear wheel 131 is further geared and engaged with a corresponding gear wheel 145 of the first spool 140. In this way, a rotative movement of the drive sleeve 40 can be directly transferred into a roll off and roll up rotation of the first spool 140.

The second spool 142 is further engaged with a spool spring 144. In this way, unwinding or unrolling the dose indicating tape 146 from the second spool 142 may take place against the action of the spool spring 144. By means of the spool spring 144 the dose indicating tape 146 can be strained and can be kept substantially free of slack. Additionally and as shown in FIG. 12, the housing comprises a support 36a to provide a basis for the flexible dose indicating tape 146.

As further indicated in FIG. 2, the first spool 140 comprises a proximally located bobbin integrally formed with a distally located bearing portion 134. The bearing portion 134 is located and supported in a cup-shaped receptacle of the insert 120, thereby forming a bearing 128 for the first spool 140. In a corresponding way also the second spool 142 can be rotatably supported in the insert 120. As indicated in FIG. 7, the respective bearing portion 136 of the second spool 142 is only partially formed by an insert portion 123 of the insert 120.

The residual portion of the respective bearing 129 is formed directly from a radially outwardly extending receptacle portion 38 of the housing 30. As further indicated in FIGS. 2 and 7, the spool spring 144 radially extends between the outer circumference of the bearing portion 136, the inside facing sidewall portions of the insert portion 123 and the receptacle portion 38 of the housing 30.

As it is further illustrated in FIG. 7, the drug delivery device 10 in an axial portion comprises a T-like shape in cross-section to accommodate the dose indicating mechanism 130, wherein the two spools 140, 142 are located in receptacle portions 37, 38 being furthest away from each other. Therebetween and on one side there extends a radially outwardly extending receptacle portion 39 of the housing 30. Opposite the receptacle portion 39, the housing 30 comprises a dose indicating window 36 through which the numbers 148 of the dose indicating tape 146 can be visualised.

The lobe-shaped receptacle portions 37, 38 and 39 of the housing 30 are almost entirely occupied with correspondingly shaped insert portions 125, 123 and 124 of the insert 120, respectively.

Here, the insert 120 may provide a mounting basis to preassemble the dose indicating mechanism 130 and to insert the entire dose indicating mechanism 130 in one step into the housing 30 during assembly of the drug delivery device 10.

As further indicated in FIG. 5, also the gear wheel 131 is rotatably supported by a pin-shaped bearing 127 of the insert 120.

As further shown in FIGS. 2 and 10, the proximal closure 32 of the housing 30 provides axial fixing of the two spools 140, 142 inside the housing 30. Hence, the two spools 140, 142 can be axially constrained by the insert 120 and by the proximal closure 32 of the housing 30.

Figure 26:
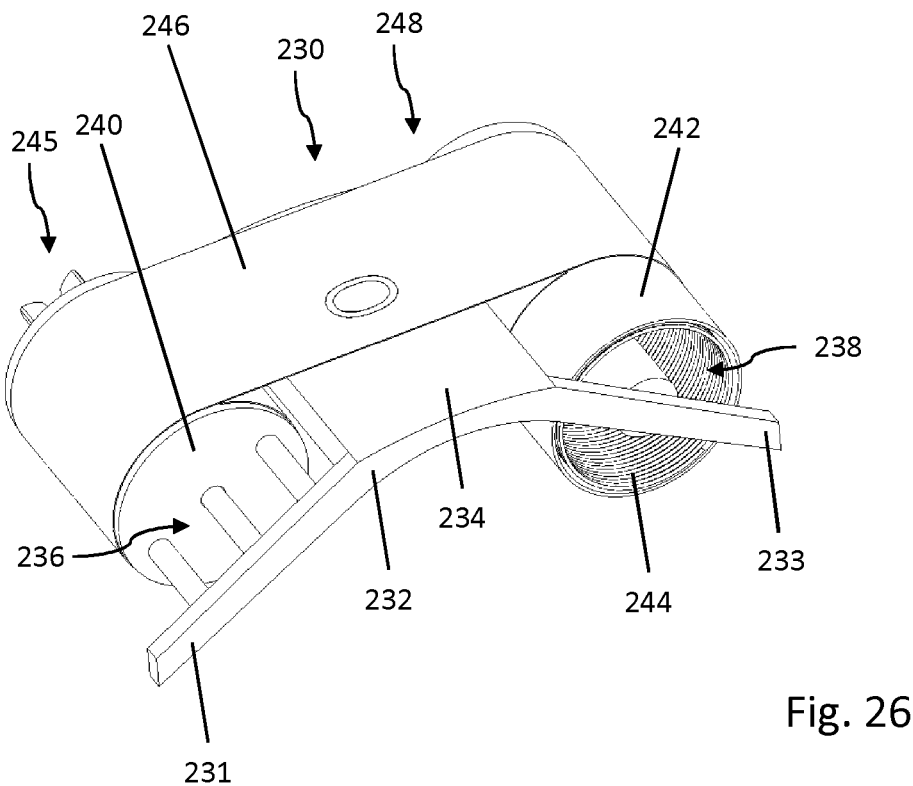
FIG. 26 shows an alternative embodiment of a dose indicating mechanism in an isolated perspective illustration and FIG. 27 shows the dose indicating mechanism according to FIG. 27 when assembled in the housing of the drive mechanism.
Figure 27:
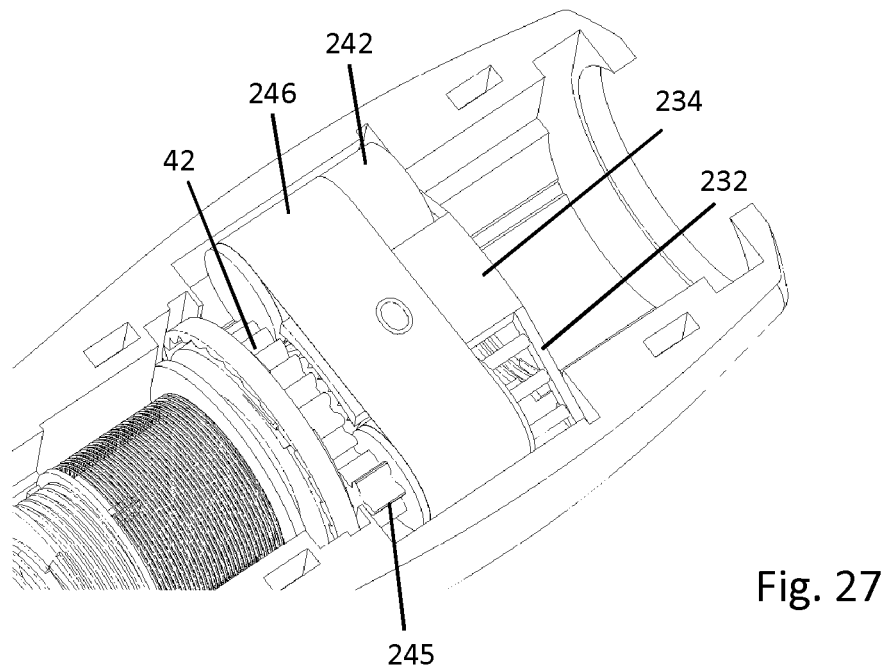

In FIGS. 26 and 27 another embodiment of a dose indicating mechanism 230 is illustrated. Here, first and second spools 240, 242 are rotatably supported on bearings 236, 238, respectively extending in distal direction from radially outwardly extending branches 231, 233 of a base 232. Between the two bearings 236, 238, the base 232 comprises and provides a rather flat shaped support section 234 in order to mechanically support the dose indicating tape 246 extending between the parallel oriented and radially separated spools 240, 242.

In the embodiment according to FIGS. 26 and 27, the second spool 242 is also engaged with a spool spring 244. However and in contrast to the embodiment as for instance shown in FIG. 2, the spool spring 244 is located inside the second spool 242. The spool spring 244 comprises a helical spring, wherein one end of the spring is connected to the second spool 242 while an opposite end is connected to the branch 233.

Also with the dose indicating mechanism 230, the first spool 240 comprises a gear wheel 245 directly engaged with the gear wheel 42 of the drive sleeve 40.

In FIGS. 2, 12 and in FIGS. 16 to 20 a last dose sleeve 100 rotatably supported in the housing 30 is shown. The last dose sleeve 100 comprises a radially outwardly extending flange portion 102 by way of which the last dose sleeve 100 axially abuts with a proximal sleeve portion 126 of the insert 120. Moreover, the last dose sleeve 100 comprises an axially extending groove 101 intersecting a rather smooth shaped outer circumference thereof.

Said groove 101 is engaged with a radially inwardly extending protrusion 107 of a last dose member 105, which is designed as a last dose nut or as a half nut. As for instance indicated in FIG. 18 the last dose member 105 comprises a semi-circular arcuate shape and features radial stop faces 108, 109 at its opposite circumferential ends. Moreover, the last dose member 105 comprises an outer thread 106 to threadedly engage with a correspondingly shaped threaded portion 33 of the housing 30. In this way, the last dose limiting member 105 is threadedly engaged with the housing 30 but is rotatably locked to the last dose sleeve 100.

Figure 4:
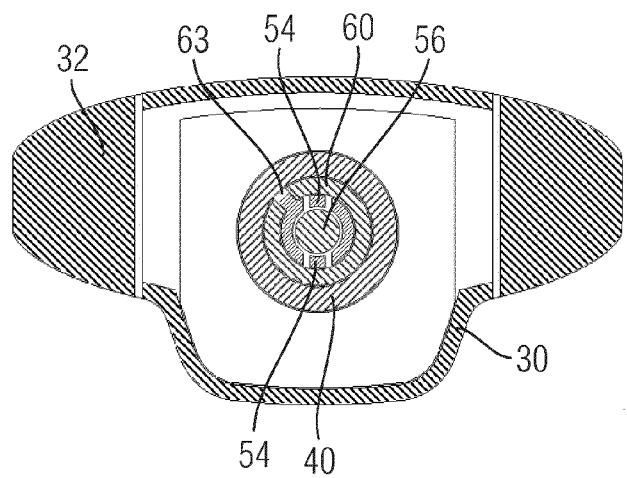
FIG. 4 shows a cross-section along B-B according to FIG. 2.
Figure 22:
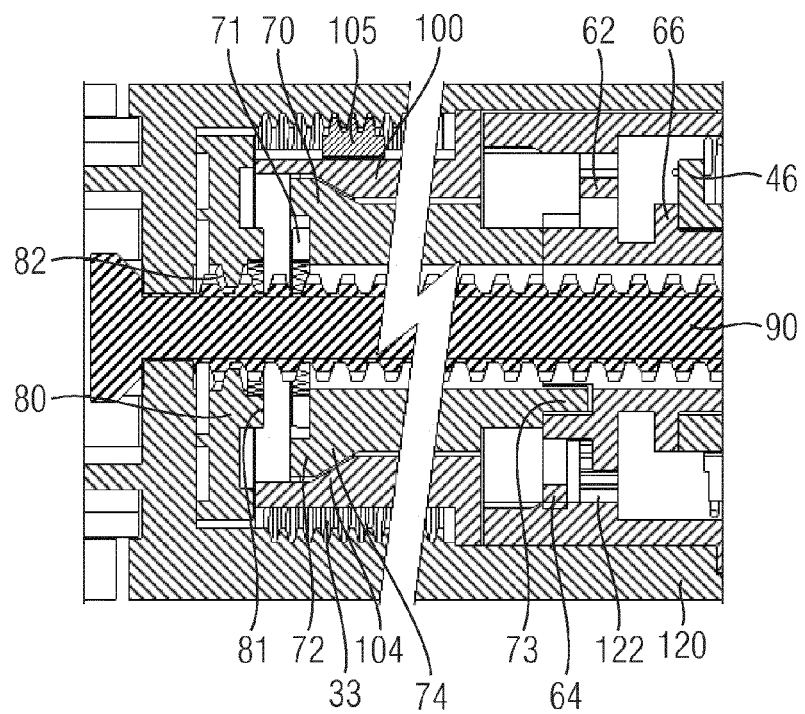
FIG. 22 shows a longitudinal cross-section through a distal clutch member in dose setting configuration.
Figure 23:
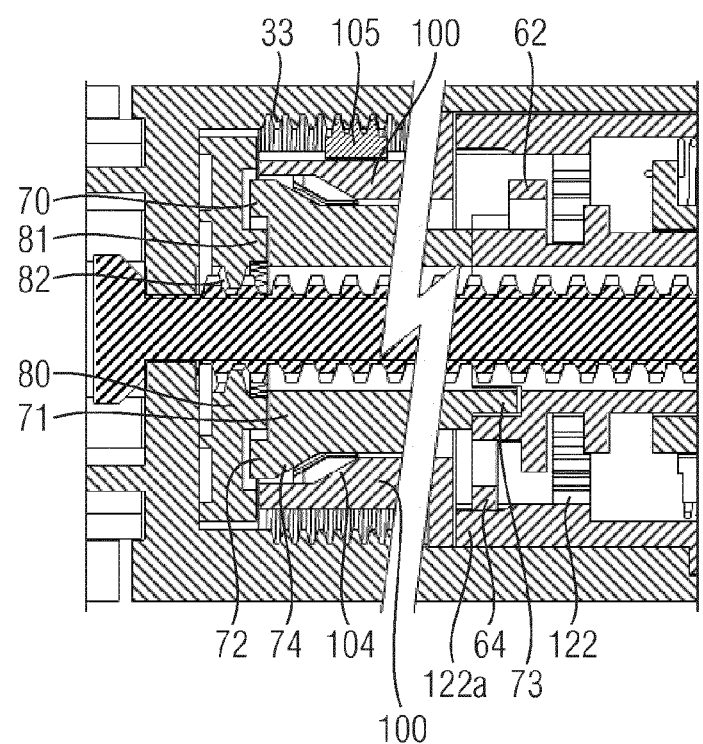
FIG. 23 shows a longitudinal cross-section of the distal clutch member in a dose dispensing configuration.

In FIGS. 1, 22 and 23 a distal clutch member 70 is illustrated, which is axially as well as rotatably engaged with the main clutch member 60. Hence, a rotation of the main clutch member 60 equally transfers to the distal clutch member 70. Moreover, also an axial displacement of the main clutch member 60 relative to the housing 30 or relative to the drive sleeve 40 is equally transferable to a respective axial displacement of the distal clutch member 70. In order to provided axial and rotational engagement between the main clutch with the distal clutch 70 and/or with the proximal clutch 50 the main clutch 60 may further exhibit a notch or groove 63 as shown in FIG. 4 to engage with a correspondingly shaped snap member of e.g. the proximal clutch 50, which is not particularly illustrated. Moreover and as indicated in the cross sections of FIGS. 9 and 22 the distal clutch member 70 comprises three circumferentially distributed snap elements 73 to axially engage with correspondingly shaped recesses of the main clutch 60.

Figure 8:
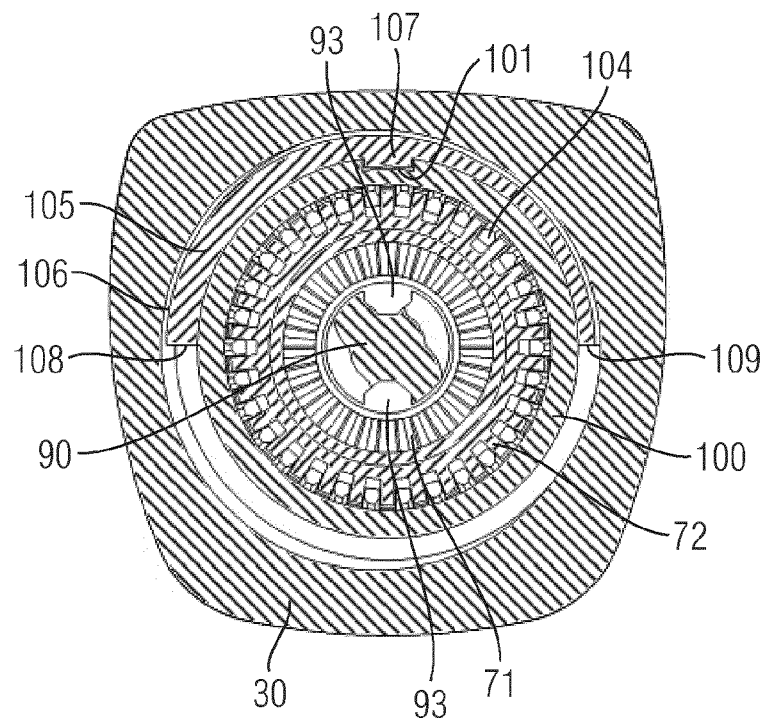
FIG. 8 shows a cross-section along F-F according to FIG. 2.

In a dose setting configuration as illustrated in FIG. 22, the distal clutch member 70 is rotatably locked to the last dose sleeve 100. As shown for instance in cross-section according to FIG. 8, the distal clutch member 70 comprises radially outwardly extending teeth 72 engaging with a correspondingly shaped toothed structure 104 at an inside facing sidewall portion of the last dose sleeve 100. In this way, a rotation of the drive sleeve 40 and hence a rotation of the clutch members 50, 60, 70 can transfer to a respective rotation of the last dose sleeve 100.

As a consequence, the last dose member 105 will travel in axial direction relative to the last dose sleeve 100 during a dose setting procedure. The lead of the threaded engagement of the last dose member 105 and the housing 30 as well as the axial elongation of the last dose sleeve 100 is designed such that a stop configuration as for instance illustrated in FIG. 19 correlates with the maximum allowable distal position of the piston rod 90 relative to the barrel 18 of the cartridge 14.

Figure 19:
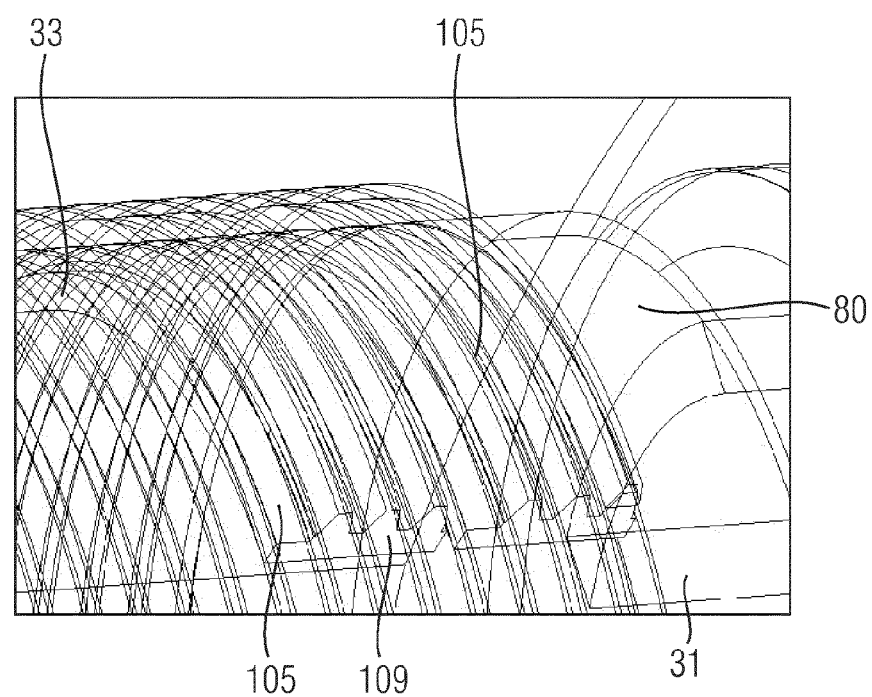
FIG. 19 shows a configuration of the last dose limiting mechanism in a last dose configuration.

In FIG. 19 mutual abutment of one of the stop faces 108, 109 with a radially inwardly extending stop 31 of the housing 30 is shown. Also here and in comparison with the single dose limiting member 110 radially extending stops 108, 109, 31 may provide a well-defined blocking of the mutually engaging components 105, 110 and housing 30.

Since the last dose sleeve 100 is only selectively coupled with the drive sleeve 40 and/or with the distal clutch member 70 during a dose setting procedure, the last dose member 105 will always rest in its axial position during a dose dispensing procedure.

Hence, during consecutive dose setting procedures, the last dose member 105 successively advances towards a last dose limiting configuration. In situations where the amount of medicament left in the cartridge 12 is less than the size of a single dose to be set during a dose setting procedure, the last dose limiting member 105 will be advanced in distal direction 1 and will engage with the radial stop 31 of the housing 30 thereby blocking a further rotation of the last dose sleeve 100 and hence of the clutches 50, 60, 70 and the dose setting member 85, accordingly. In this way it can be effectively prevented that a user selects and dials a dose exceeding the amount of medicament left in the cartridge 14.

In the following, dispensing of a dose is described.

Figure 17:
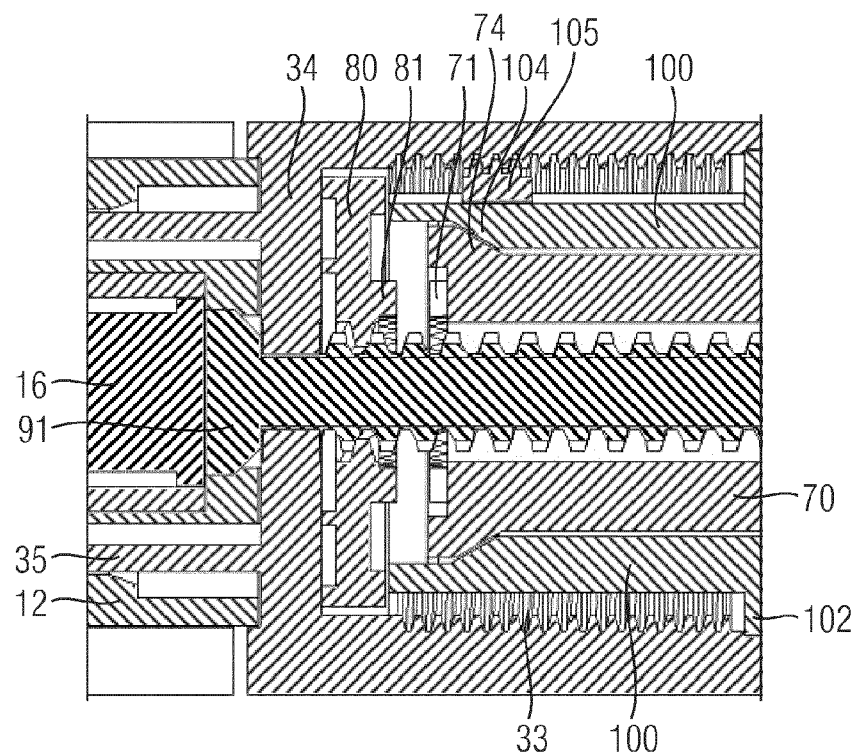
FIG. 17 shows an enlarged longitudinal cross-section through the last dose limiting mechanism.
Figure 18:
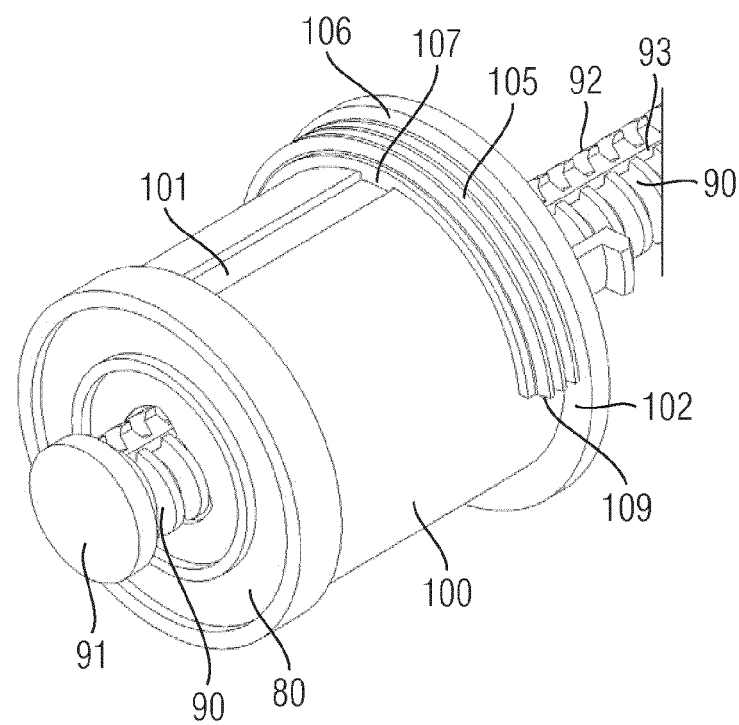
FIG. 18 shows another perspective view of the last dose limiting mechanism in a zero dose configuration.

As shown in FIG. 17, the piston rod or lead screw 90 operably engaged with a proximal end face of the piston 16 of the cartridge 14 is axially guided by the radially inwardly extending support 34 or web of the housing 30. As shown in cross section in FIG. 8, the piston rod 90 not only comprises an outer thread 92 but also two diametrically opposite and axially extending grooves 93. By means of said grooves 93 the piston rod 90 is rotatably locked to the housing 30. Hence, the piston rod 90 is splined to the housing 30. The piston rod 90 further comprises a radially widening pressure piece 91 or a pressure foot at its distal end in order to homogeneously transfer axially directed thrust to the piston 16 of the cartridge 14 during dose dispensing.

The piston rod 90 is further threadedly engaged with a drive wheel 80 comprising an inner thread 82 engaged with the outer thread 92 of the piston rod 90. Due to the threaded engagement with the drive wheel 80 and the splined engagement with the housing 30, the piston rod 90 experiences a distally directed translational displacement when the drive wheel 80 rotates in a dose decrementing direction 5 during dose dispensing. In order to transfer a dose dispensing torque to the drive wheel 80 or drive nut the drive wheel 80 comprises a crown wheel portion 81 at its proximally facing side to engage with a correspondingly shaped crown wheel portion 71 of the distal clutch member 70.

By displacing the distal clutch member 70 in distal direction 1 the mutually corresponding crown wheel portions 71, 81 of distal clutch member 70 and drive wheel 80 mutually engage. In this way, a rotation of the distal clutch member 70 can be equally transferred to a rotation of the drive wheel 80, which transfers to a distally directed displacement of the piston rod 90.

Figure 20:
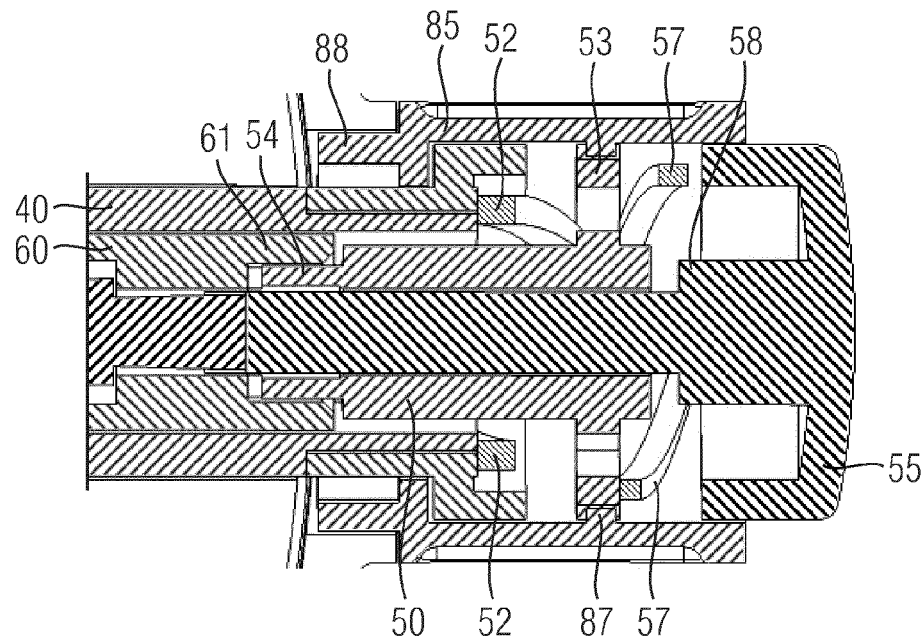
FIG. 20 shows a longitudinal cross-section through the proximal end of the drive mechanism in a dose setting configuration.
Figure 21:
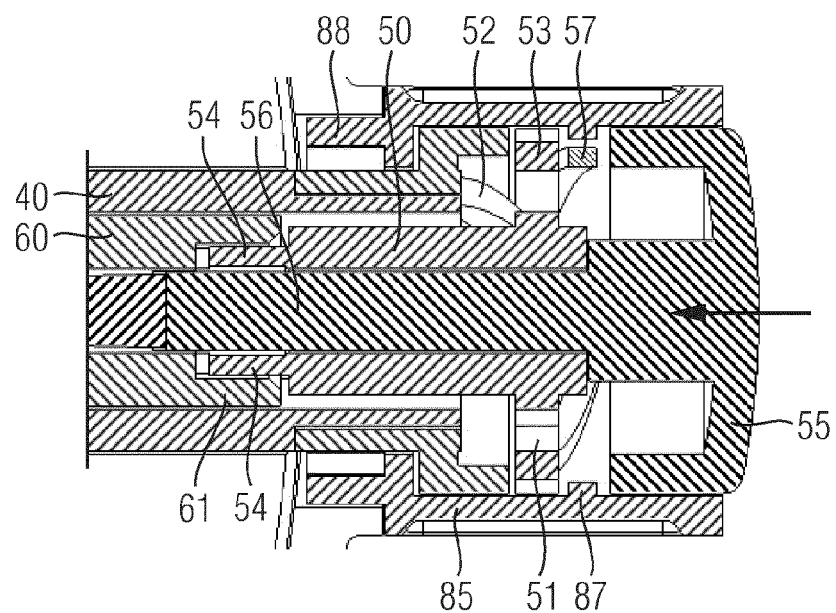
FIG. 21 shows a proximal end of the drive mechanism in a dose dispensing configuration.

A distally direction displacement of the distal clutch member 70 can be attained by depressing the dose dispensing button 55 in distal direction 1 as indicated by a comparison of FIGS. 20 and 21. The dose dispensing button 55 comprising a shaft portion 56 extending into the hollow shaft portion of the proximal clutch member 50 is displaceable in distal direction 1 until a stepped portion 58 radially outwardly extending from the shaft portion 56 axially abuts with a proximal end of the proximal clutch member 50.

In this way, axially and distally directed displacement of the dose dispensing button 55 against the action of an integrated spring 57 can be transferred into a respective distally directed displacement of the mutually engaging clutch members 50, 60 and 70. Since the clutch members 50, 60 and 70 are axially engaged in both directions, the proximal clutch member 50 can be displaced in distal direction 1 against the action of another integrated spring 52, which axially abuts with a proximal end face of the drive sleeve 40 and/or with a stepped portion of the dose setting member 85.

Distally directed displacement of the proximal clutch member 50 relative to the dose setting member 85 also disengages the protrusions 87 and the geared rim 53. In the dose dispensing configuration as shown in FIG. 21, the dose setting member 58 is therefore substantially functionless. It may be rotated in any direction without having connection to the proximal clutch member 50.

The proximal clutch member 50 is depressible in distal direction 1 against the action of the spring 52. Since the proximal clutch member 50 is axially engaged with the main clutch member 60, e.g. by means of a snap fit engagement, and since the main clutch member 60 is also axially connected with the distal clutch member 70, a release of the dose dispensing button 55 allows and induces a proximally directed return motion of the proximal clutch member 50 under the effect of the relaxing spring 52.

In this way, the distal clutch member 70 can be selectively engaged and disengaged with the drive wheel 80. Moreover, by means of the integrated spring 57 also the dose dispensing button 55 will return into its initial proximal end configuration in which the dose dispensing button 55 at least partially extends from the proximal end face of the dose setting member 85.

As shown in FIG. 20, the integrated spring 57 of the dose dispensing button 55 axially abuts against a radially outwardly extending flange portion 51 of the proximal clutch member 50.

By means of a distally directed displacement of the distal clutch member 70 the distal clutch member 70 not only rotatably locks to the drive wheel 80 but also disengages from the last dose sleeve 100 as becomes apparent from a comparison of FIGS. 22 and 23. As illustrated there, the last dose sleeve 100 comprises an inclined or tapered toothed structure 104 at its inner circumference near its distal end. Accordingly, the distal clutch member 70 comprises a correspondingly shaped inclined toothed portion 74 to engage with the toothed portion 104 of the last dose sleeve 100 when in dose setting configuration, hence when the distal clutch member 70 is in its proximal stop position.

As further indicated in FIG. 22 the ratchet member 62 of the main clutch 60 is rotatably locked to the toothed ring portion 122 of the insert 120. Additionally and as shown in FIG. 22 the main clutch 60 comprises a radially outwardly extending flange 66 which serves as a stop to engage with a distal end face of the drive sleeve 40. In this way the proximally directed displacement of the main clutch 60 under the effect of the springs 52, 57 can be delimited.

By displacing the three clutch members 50, 60, 70 simultaneously in distal direction 1, the crown wheel portion 71 of the distal clutch member 70 will engage with the corresponding crown wheel portion 81 of the drive wheel 80 before the ratchet member 62 disengages from the toothed ring portion 122 of the insert 120. The mutual engagement of the two crown wheel portions 71, 81 is designed such, that at least a further distally directed displacement of the distal clutch member 70 towards the drive wheel 80 is still possible when the distal clutch member 70 and the drive wheel 80 are already rotatably coupled.

During this further distally directed displacement of the distal clutch member 70 and when reaching the distal stop configuration, the ratchet member 62 displaces or has displaced in distal direction 1 relative to the toothed ring 122 and is then no longer inhibited to rotate under the action of the relaxing helical spring 48. As indicated in FIG. 23, the ratchet member 62 is disengaged from the insert 120 and hence it is effectively released from the housing 30.

The main clutch member 60 further comprises a pawl-shaped clicking member 64 as illustrated in FIGS. 9 and 23. Said clicking member 64 is arranged axially offset from the ratchet member 62. It may engage with another recessed structure 122a featuring numerous and equidistantly arranged recesses 122a located on the inside facing wall of the insert 120 when reaching the dose dispensing configuration as illustrated in FIG. 23.

The clicking member 64 is oriented symmetrically to the ratchet member 62 and engages with the recess structure 122a when the ratchet member 62 disengages from the toothed ring 122. Since the main clutch member 60 is now allowed to rotate in a dose decrementing direction 5 the clicking member 64 is operable to generate a frequent clicking sound when meshing with the recessed structure 122a, thereby audibly indicating to a user, that a dose dispensing procedure is in progress.

Moreover the clicking member 64 and the recessed structure 122a of the insert 120 may be shaped and designed in such a way that only a rotation in dose decrementing direction 5 is allowed while an oppositely directed rotation in dose incrementing direction 4 of the distal clutch 60 relative to the insert 120 and hence relative to the housing 30 is effectively blocked. In this way the clicking member 64 and the recessed structure 122a act as a further ratchet mechanism operable to impede a proximally directed displacement of the piston rod 90.

In order to provide a substantially slipless switching from dose setting mode to the dose dispensing mode and vice versa, the distal clutch member 70 engages with the drive wheel 80 before the main clutch member 60 disengages from the insert 120 or housing 30. Also in the event of a premature release of the dose dispensing button 55 during a dose dispensing procedure, a rotational interlock of the main clutch member 60 with the insert 120 will be re-established before distal clutch member 70 and drive wheel 80 become operably disengaged.

Since the drive sleeve 40 rotates in dose decrementing direction 5 during dose dispensing also the dose limiting member 110 will return into its initial configuration, i.e. in a zero dose configuration, in which the second stop 114 of the dose limiting member 110 engages with a radially extending second stop 44 of the drive sleeve 40.

Moreover, and as shown in FIG. 6, the dose limiting member 110 comprises a circumferentially extending clicking member 115 operable to audibly engage with a ledge 45 provided at a recess 49 of the drive sleeve 40. Here, the pawl-like clicking member 115 is biased radially inwardly so as to generate a click sound before or just when a zero dose configuration as illustrated in FIG. 6 is reached. Since the dose limiting member 110 travels in proximal direction 2 during dose incrementing rotation and travels in distal direction 1 during dose dispensing the audible click sound provided by the mutual engagement of the clicking member 115 with the ledge 45 is indicative to a user, that a dose dispensing procedure just terminates.

Accordingly and since the drive sleeve 40 is permanently engaged with the gear wheels 145, 245 of respective dose indicating mechanisms 130, 230, the numbers 148, 248 of the dose indicating tape 146, 246 that show up in the dose indicating window 36 will continuously count down until a zero dose configuration coinciding with the mutual engagement of the second stops 114, 44 is reached.

Moreover, as can be seen from the longitudinal cross-section according to FIG. 2, the drive wheel 80 is axially constrained between the radially inwardly extending protrusions 34 of the housing and the last dose sleeve 100, which itself is in axial abutment with the distal sleeve portion 126 of the insert 120. In this way, fixing of the insert 120 in the housing 30 effectively fixes the last dose sleeve 100 and the drive wheel 80 in axial direction inside the housing 30.

Moreover, the insert 120 itself can be axially fixed in the housing 30 by means of the two spools 140, 142 extending axially between the bearing portion 128, 129 of the insert 120 and the proximal closure 32 of the housing 30.

As further shown in FIGS. 2 and 17, the housing 30 also comprises a distally extending appendix 35 extending in distal direction from the radially inwardly extending support 34. As indicated in FIG. 17, said appendix 35 may be operable to connect the proximal housing 30 with the cartridge holder 12. Cartridge holder 12 and housing 30 may either be releasably connected in order to provide a reusable drug delivery device, allowing to replace an empty cartridge 14 by a new one.

Alternatively, the drug delivery device 10 may also be designed as a disposable device, wherein cartridge holder 12 and proximal housing 30 are typically inseparably connected.

The present design and assembly of the components of the drive mechanism 3 allow for an axial adjustment of the piston rod 90 during a final step of assembly. In particular, prior to a final assembly of the dose dispensing button 55, effectively closing the housing 30 in proximal direction 2, the piston rod 90 is accessible by e.g. introducing an adjustment rod (not illustrated) through the hollow assembly of proximal clutch 50 and main clutch 60. In this way the piston rod 90 can be pushed in distal direction 1 to get in direct abutment with the piston 16 of the cartridge 14. In this way a conventional priming procedure typically to be executed by the end user prior to an initial use of the device 10 may become substantially superfluous.

LIST OF REFERENCE NUMERALS 1 distal direction
2 proximal direction
3 drive mechanism
4 dose incrementing direction
5 dose decrementing direction
10 drug delivery device
12 cartridge holder
14 cartridge
16 piston
18 barrel
20 needle assembly
22 needle hub
24 needle cap
25 needle
26 protective cap
30 housing
31 radial stop
32 closure
33 threaded portion
34 protrusion
35 appendix
36 dose indicating window
36a support 37 receptacle portion
38 receptacle portion
39 receptacle portion
40 drive sleeve
41 threaded portion
42 gear wheel
43 groove
44 radial stop
45 ledge
46 spring mount
47 radial stop
48 spring
49 recess
50 proximal clutch member
51 flange portion
52 spring
53 geared rim
54 fastening element
55 dose dispensing button
56 shaft portion
57 spring
58 step portion
60 main clutch member
61 fastening member
62 ratchet member
63 groove
64 clicking member
66 flange portion
70 distal clutch member
71 crown wheel portion
72 tooth
73 snap element
74 inclined toothed portion
80 drive wheel
81 crown wheel portion
82 inner thread
85 dose setting member
86 rippled structure
87 protrusion
88 projection
90 piston rod
91 pressure piece
92 thread
93 groove
100 last dose sleeve
101 groove
102 flange portion
103 end face
104 toothed structure
105 last dose member
106 outer thread
107 protrusion
108 stop face
109 stop face
110 dose limiting member
111 inner thread
112 protrusion
113 radial stop
114 stop
115 clicking member
120 insert
121 recess
122 toothed ring
122a recessed structure
123 insert portion
124 insert portion
125 insert portion
126 sleeve portion
127 bearing
128 bearing
129 bearing
130 dose indicating mechanism
131 gear wheel
132 sprocket
134 bearing portion
136 bearing portion
140 spool
142 spool
144 spool spring
145 gear wheel
146 dose indicating tape
148 number
230 dose indicating mechanism
231 branch
232 base
233 branch
234 support section
236 bearing
238 bearing
240 spool
242 spool
244 spool spring
245 gear wheel
246 dose indicating tape
248 number

The invention claimed is:

1. A drug delivery device for dispensing a dose of a medicament, the drug delivery device comprising:
an elongate housing;
a cartridge arranged in the housing, the cartridge comprising the medicament and a piston to displace the medicament;
a piston rod configured to engage the piston to displace the piston in a distal direction along a longitudinal axis of the housing;
a dose indicating mechanism comprising a first spool and a second spool rotatably supported in the housing, the first spool and the second spool being oriented substantially parallel to each other and substantially parallel to the piston rod;
a dose indicating tape having a first end fixed to an outer circumference of the first spool and a second end fixed to an outer circumference of the second spool, the dose indicating tape being coiled onto at least the second spool; and
a drive sleeve coaxial, along the longitudinal axis, with the piston rod, the drive sleeve being selectively engageable with a user-operable dose setting member and selectively engageable with a user-operable dose dispensing button.

2. The drug delivery device of claim 1, wherein the drive sleeve is positioned between the first spool and the second spool such that the dose indicating tape extends across the drive sleeve, the drive sleeve being operable to set the dose of the medicament and being rotatable to displace the piston rod in the distal direction, wherein the drive sleeve comprises a gear wheel engaged with a gear wheel of the first spool such that the first spool is rotatably engaged with the drive sleeve.

3. The drug delivery device of claim 1, wherein the first spool and the second spool are rotatable about axes substantially parallel to the longitudinal axis, and the longitudinal axis is between the axes.

4. A drive mechanism of a drug delivery device for dispensing a dose of a medicament, the drive mechanism comprising:
- a piston rod configured to engage with a piston of a cartridge to displace the piston in a distal direction along a longitudinal axis of a housing of the drug delivery device;
- a dose indicating mechanism comprising a first spool and a second spool configured to be rotatably supported in the housing, the first spool and the second spool being oriented substantially parallel to each other and substantially parallel to the piston rod when rotatably supported in the housing;
- a dose indicating tape having a first end fixed to an outer circumference of the first spool and a second end fixed to an outer circumference of the second spool, the dose indicating tape being coiled onto at least the second spool; and
- a drive sleeve coaxial, along the longitudinal axis, with the piston rod, the drive sleeve being selectively engageable with a user-operable dose setting member and selectively engageable with a user-operable dose dispensing button.

5. The drive mechanism of claim 4, wherein the drive sleeve is operable to set the dose of the medicament to be ejected from the drug delivery device, the first spool being rotatably engaged with the drive sleeve.

6. The drive mechanism of claim 5, wherein the drive sleeve is positioned between the first spool and the second spool such that the dose indicating tape extends across the drive sleeve.

7. The drive mechanism of claim 5, wherein the first spool comprises a gear wheel engaged with a gear wheel of the drive sleeve.

8. The drive mechanism of claim 7, wherein the gear wheel of the drive sleeve is distally offset from the dose indicating tape.

9. The drive mechanism of claim 7, wherein the gear wheel of the first spool is directly engaged with the gear wheel of the drive sleeve.

10. The drive mechanism of claim 4, further comprising a support member positioned between the first spool and the second spool, the support member configured to support the dose indicating tape, and the dose indicating tape extending from the first spool across the support member to the second spool.

11. The drive mechanism of claim 4, wherein at least one of the first spool or the second spool comprises a bearing portion offset from the dose indicating tape along the longitudinal axis, the bearing portion being rotatably arranged in an axially extending bearing recess of the housing.

12. The drive mechanism of claim 11, wherein at least one of the first spool or the second spool is axially constrained by the bearing recess and a proximal closure of the housing.

13. The drive mechanism of claim 11, further comprising a spool spring positioned radially between the bearing portion and the bearing recess, wherein the second spool is rotatable in a dose incrementing direction against a biasing force of the spool spring and in a dose decrementing direction with the biasing force of the spool spring.

14. The drive mechanism of claim 13, wherein the spool spring comprises a helical spring having a first end engaged with the housing and a second end engaged with the second spool.

15. The drive mechanism of claim 13, wherein the second spool is hollow, and the spool spring is located inside of the second spool.

16. The drive mechanism of claim 15, wherein the first spool and the second spool are rotatably supported on an insert fixable in the housing.

17. The drive mechanism of claim 4, wherein the first spool and the second spool are rotatable about axes substantially parallel to the longitudinal axis, and the longitudinal axis is between the axes.

* * * * *